(12) United States Patent
Shimizu et al.

(10) Patent No.: US 10,100,030 B2
(45) Date of Patent: Oct. 16, 2018

(54) CARBOXYMETHYL PIPERIDINE DERIVATIVE

(71) Applicant: Kissei Pharmaceutical Co., Ltd., Matsumoto-shi, Nagano (JP)

(72) Inventors: Kazuo Shimizu, Azumino (JP); Takashi Miyagi, Azumino (JP); Kohsuke Ohno, Azumino (JP); Yasunori Ueno, Azumino (JP); Yusuke Onda, Azumino (JP); Hikaru Suzuki, Azumino (JP)

(73) Assignee: KISSEI PHARMACEUTICAL CO., LTD., Matsumoto-shi, Nagano (JP)

( * ) Notice: Subject to any disclaimer, the term of this patent is extended or adjusted under 35 U.S.C. 154(b) by 0 days.

(21) Appl. No.: 15/034,808

(22) PCT Filed: Nov. 6, 2014

(86) PCT No.: PCT/JP2014/079384
§ 371 (c)(1),
(2) Date: May 5, 2016

(87) PCT Pub. No.: WO2015/068744
PCT Pub. Date: May 14, 2015

(65) Prior Publication Data
US 2016/0289206 A1   Oct. 6, 2016

(30) Foreign Application Priority Data
Nov. 8, 2013  (JP) ................................ 2013-231773

(51) Int. Cl.
*C07D 401/04*  (2006.01)
*C07D 413/14*  (2006.01)

(52) U.S. Cl.
CPC ......... *C07D 401/04* (2013.01); *C07D 413/14* (2013.01)

(58) Field of Classification Search
CPC ............................ C07D 401/04; C07D 413/14
See application file for complete search history.

(56) References Cited

U.S. PATENT DOCUMENTS

| | | | |
|---|---|---|---|
| 6,225,316 B1 | 5/2001 | Bos et al. |
| 6,297,375 B1 | 10/2001 | Bos et al. |
| 6,479,483 B2 | 11/2002 | Bos et al. |
| 6,576,762 B2 | 6/2003 | Hoffmann et al. |
| 6,593,472 B2 | 7/2003 | Hoffmann et al. |
| 6,770,637 B2 | 8/2004 | Godel et al. |
| 6,849,624 B2 | 2/2005 | Ballard et al. |
| 7,211,579 B2 | 5/2007 | Funk et al. |
| 7,683,056 B2 | 3/2010 | Alvaro et al. |
| 7,939,533 B2 | 5/2011 | Hoffmann et al. |
| 8,344,005 B2 | 1/2013 | Alvaro et al. |
| 8,426,450 B1 | 4/2013 | Fadini et al. |
| 2002/0091265 A1 | 7/2002 | Bos et al. |
| 2003/0004157 A1 | 1/2003 | Buser et al. |
| 2003/0083345 A1 | 5/2003 | Hoffmann et al. |
| 2005/0090533 A1 | 4/2005 | Hoffmann et al. |
| 2006/0030600 A1 | 2/2006 | Schnider |
| 2007/0071813 A1 | 3/2007 | Ahmed et al. |

FOREIGN PATENT DOCUMENTS

| | | |
|---|---|---|
| EP | 1 103 545 A1 | 5/2001 |
| GB | 2347422 A | 9/2000 |
| WO | 2005/002577 A1 | 1/2005 |
| WO | 2007121280 A1 | 10/2007 |
| WO | 2008019372 A2 | 2/2008 |
| WO | 2011/054773 A1 | 5/2011 |
| WO | 2013/082102 A1 | 6/2013 |

OTHER PUBLICATIONS

International Search Report dated Dec. 16, 2014, issued in counterpart International Application No. PCT/JP2014/079384 (2 pages).
Office Action, dated Jun. 22, 2018, in counterpart Russian patent application No. 2016122464 (w/ English translation; 12 pages).

*Primary Examiner* — Umamaheswari Ramachandran
(74) *Attorney, Agent, or Firm* — Westerman, Hattori, Daniels & Adrian, LLP

(57) ABSTRACT

The present invention provides a new compound which has $NK_1$ receptor antagonist activity, whose CYP3A4 inhibitory activity is reduced compared to aprepitant, and which are useful for the prevention or treatment of cancer-chemotherapy-induced nausea and vomiting. That is, the present invention relates to carboxymethyl piperidine derivatives represented by the following formula (I) or a pharmaceutically acceptable salt thereof. Wherein, ring A is a benzene ring or the like; ring B is a pyridine ring or the like; $R_1$ is $C_{1-6}$ alkyl or $C_{1-6}$ alkoxy; $R_2$ and $R_3$ are a hydrogen atom or methyl; and n is an integral number from 0 to 5.

Formula (I)

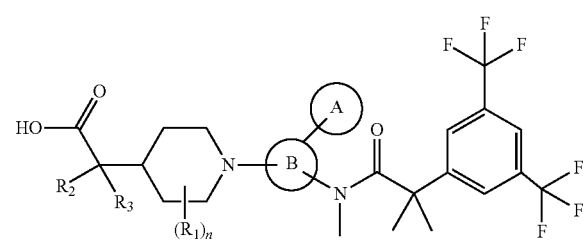

22 Claims, 1 Drawing Sheet
Specification includes a Sequence Listing.

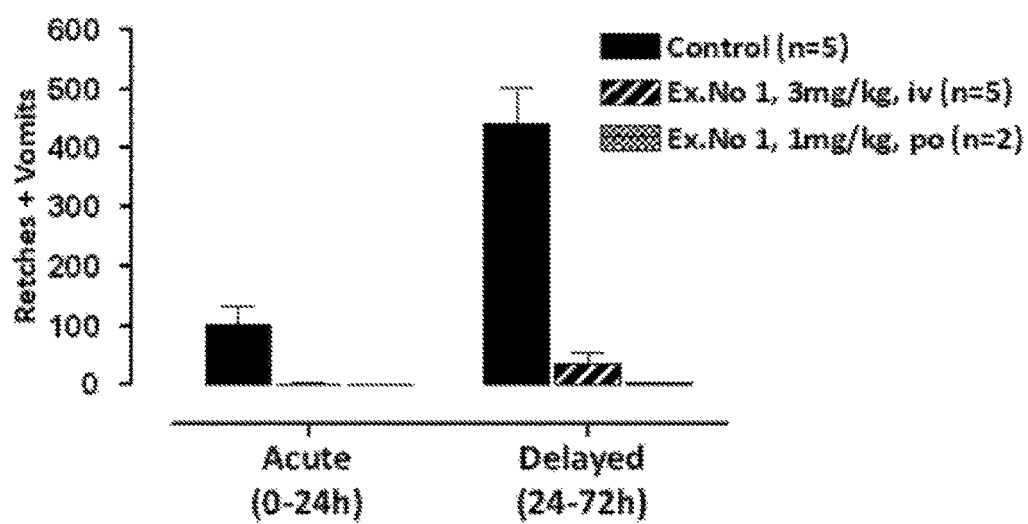

CARBOXYMETHYL PIPERIDINE DERIVATIVE

TECHNICAL FIELD

The present invention relates to carboxymethyl piperidine derivatives useful as medicaments.

More particularly, the present invention relates to carboxymethyl piperidine derivatives or pharmaceutically acceptable salts thereof which have substance P/neurokinin 1 ($NK_1$) receptor antagonist activity, and which are useful as agents for the prevention or treatment of cancer-chemotherapy-induced nausea and vomiting (CINV) and so on.

BACKGROUND ART

CINV occurs when the vomiting center located in the lateral reticular formation of the medulla oblongata receives a stimulus. The area postrema and the solitary nucleus of the medulla oblongata contain $NK_1$ receptors, and the $NK_1$ receptors are believed to be closely involved in vomiting.

Administration of an antineoplastic agent facilitates the serotonin secretion from the enterochromaffin (EC) cells in the digestive tract, and serotonin directly stimulates the vomiting center through 5-hydroxytryptamine$_3$ (5-$HT_3$) receptors in the digestive tract. Also, when serotonin stimulates the vomiting center through the chemoreceptor trigger zone (CTZ) located in the area postrema of the fourth ventricle, nausea and vomiting occur. Substance P, like serotonin, is found in the EC cells in the digestive tract, and its secretion is promoted by administration of an antineoplastic agent. Recently it has been revealed that substance P induces vomiting through the $NK_1$ receptors in the CTZ or by binding to the $NK_1$ receptors in the central nervous system, and therefore $NK_1$ receptors have been attracting attention as the target for developing antiemetic agents (Non-patent literature 1).

Aprepitant is the first selective $NK_1$ receptor antagonist in the world which was approved as a preventive agent for nausea and vomiting associated with administration of antineoplastic agents. Regarding the mechanism of action of aprepitant, it is believed that aprepitant selectively inhibits the binding of substance P and the $NK_1$ receptors in the central nervous system, which is one of the pathways that induce CINV, and thus prevents CINV. Aprepitant has been launched as a preventive agent for CINV (Non-patent literature 2).

It is known that aprepitant is metabolized by cytochrome P450 (CYP) 3A4. Also, aprepitant is known to have a dose-dependent inhibitory effect on CYP3A4, a CYP3A4-inducing effect and a CYP2C9-inducing effect. Accordingly, aprepitant may cause the drug-drug interactions with drugs that inhibit or induce CYP3A4 or with drugs that are metabolized by CYP3A4 or CYP2C9. For example, it is reported that the inhibitory effect of aprepitant on CYP3A4 sometimes inhibits the metabolism of dexamethasone and that the dose should be thus adjusted when dexamethasone is combined with aprepitant (Non-patent literature 3).

Therefore, when aprepitant is used, sufficient care should be directed to the drug-drug interactions based on the inhibitory effect of aprepitant on CYP3A4.

For the above reasons, a novel $NK_1$ receptor antagonist with fewer drug-drug interactions is required in the prevention or treatment of CINV.

Compounds with an $NK_1$ receptor antagonist activity such as casopitant, netupitant, ezlopitant, rolapitant, vestipitant, vofopitant and so on, are known.

However, casopitant is reported to have an inhibitory effect on CYP3A4 and cause the drug-drug interactions due to the effect (Non-patent literature 4). Clinical trials on casopitant, as a preventive agent for cancer-chemotherapy-induced nausea and vomiting, had been conducted in the U.S. and Europe; however, its development was discontinued after the application. Netupitant is currently under development as a preventive agent for cancer-chemotherapy-induced nausea and vomiting; however, netupitant is reported to have an inhibitory effect on CYP3A4 and cause the drug-drug interactions due to the effect (Non-patent literature 5). Clinical trials on ezlopitant, as a preventive agent for cancer-chemotherapy-induced nausea and vomiting, had been conducted in the U.S.; however, its development was discontinued. Clinical trials on vofopitant, as a preventive agent for cancer-chemotherapy-induced nausea and vomiting, had been conducted in Europe; however, its development was discontinued.

Many of the above compounds resulted in the discontinuance.

Pyridine derivatives claiming to be having $NK_1$ receptor antagonist activity are described in Patent literature 1 to 16. And, prodrugs of pyridine derivatives are described in Patent literature 17 and 18.

However, carboxymethyl piperidine derivatives of the present invention are not described in the above literatures.

CITATION LIST

Patent Literature

Patent literature 1: U.S. Pat. No. 6,479,483
Patent literature 2: U.S. Pat. No. 6,770,637
Patent literature 3: U.S. Pat. No. 7,939,533
Patent literature 4: European Patent No. 1,103,545
Patent literature 5: U.S. Pat. No. 7,211,579
Patent literature 6: U.S. Patent Publication No. 2006/0030600
Patent literature 7: U.S. Pat. No. 6,576,762
Patent literature 8: U.S. Pat. No. 6,225,316
Patent literature 9: U.S. Pat. No. 7,683,056
Patent literature 10: U.S. Pat. No. 8,344,005
Patent literature 11: International publication No. WO2011/054773
Patent literature 12: U.S. Patent Publication No. 2007/0071813
Patent literature 13: U.S. Patent Publication No. 2003/0083345
Patent literature 14: U.S. Patent Publication No. 2003/0004157
Patent literature 15: U.S. Pat. No. 6,849,624
Patent literature 16: U.S. Pat. No. 6,297,375
Patent literature 17: U.S. Pat. No. 6,593,472
Patent literature 18: U.S. Pat. No. 8,426,450

Non-Patent Literature

Non-patent literature 1: P. J. Hesketh et al., European Journal of Cancer, 2003, Vol. 39, pp. 1074-1080
Non-patent literature 2: Toni M. Dando et al., Drugs, 2004, Vol. 64, No. 7, pp. 777-794
Non-patent literature 3: Jacqueline B. McCrea et al., CLINICAL PHARMACOLOGY & THERAPEUTICS, 2003, Vol. 74, No. 1, pp. 17-24
Non-patent literature 4: Stefano Zamuner et at., British Journal of Clinical Pharmacology, 2010, Vol. 70, No. 4, pp. 537-546

Non-patent literature 5: Corinna Lanzarotti et al., Support Care Cancer, 2013, Vol. 21, No. 10, pp. 2783-2791

SUMMARY OF THE INVENTION

Problem to be Solved by the Invention

A problem of the present invention is to provide as new compound which has $NK_1$ receptor antagonist activity whose CYP3A4 inhibitory activity is reduced compared to aprepitant, and which are useful for the prevention or treatment of cancer-chemotherapy-induced nausea and vomiting. A problem of the present invention is preferably to provide the above compound whose central transportation property and long-acting medicinal effect is excellent.

Means for Solving the Problem

The present invention relates to a compound represented by the following formula (I) or a pharmaceutically acceptable salt thereof.

That is, the present invention relates to the following [1] to [12] and the like.

[1] A compound represented by the formula (I):

[Chem. 1]

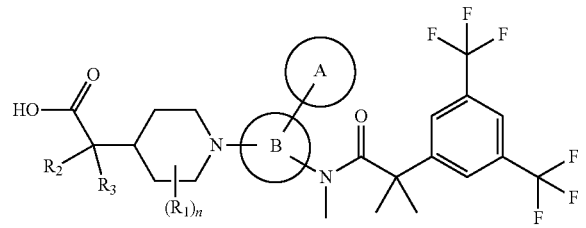

(I)

wherein
ring A is a group represented by the formula:

[Chem. 2]

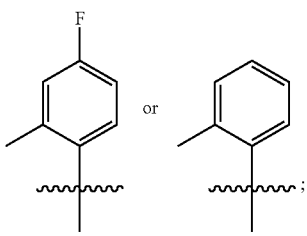

ring B is a group represented by the formula:

[Chem. 3]

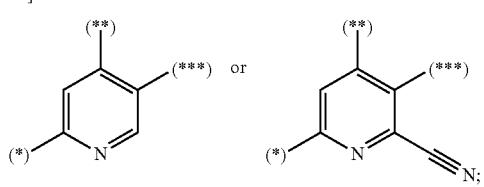

with the proviso that bonds with (*) are bonding site to the formula:

[Chem. 4]

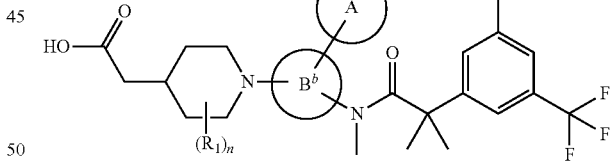

bonds with (**) are bonding site to the ring A;
bonds with (***) are bonding site to the formula:

[Chem. 5]

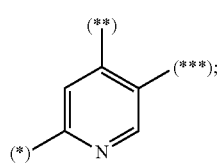

$R_1$ is $C_{1-6}$ alkyl or $C_{1-6}$ alkoxy;
$R_2$ and $R_3$ are each independently a hydrogen atom or methyl;
n is 0, 1, 2, 3, 4 or 5;
or a pharmaceutically acceptable salt thereof.

[2] The compound represented by the formula (Ia) according to the above [1]:

[Chem. 6]

(Ia)

wherein
ring A, $R_1$ and n have the same meaning as described in the above [1];
ring $B^b$ is a group represented by the formula:

[Chem. 7]

wherein, bond with (*) is a bonding site to the formula:

[Chem. 8]

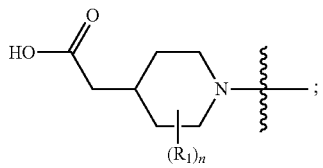

() and (*) have the same meaning as described in the above [1];
or a pharmaceutically acceptable salt thereof.
[3] The compound represented b the formula (Ib) according to the above [2]:

[Chem. 9]

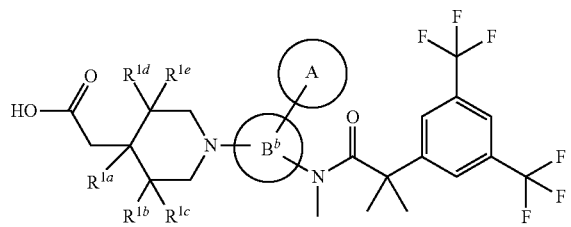

wherein
ring A and ring $B^b$ have the same meaning as described in the above [2];
with the proviso that bond with (*) is a bonding site to the formula:

[Chem. 10]

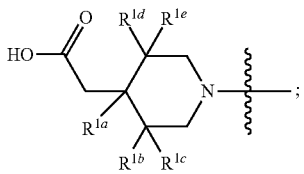

() and (*) have the same meaning as described in the above [2];
$R^{1a}$, $R^{1b}$, $R^{1c}$, $R^{1d}$ and $R^{1e}$ are each independently any one of a hydrogen atom, methyl or methoxy;
or a pharmaceutically acceptable salt thereof.
[4] The compound according to the above [1], wherein ring B is the following formula:

[Chem. 11]

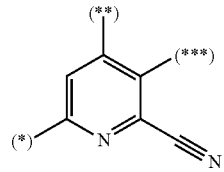

wherein, (*), () and (*) have the same meaning as described in the above [1];
or a pharmaceutically acceptable salt thereof.
[5] The compound according to the above [4], wherein $R_1$ is methyl, and n is 0 or 1, or a pharmaceutically acceptable salt thereof.
[6] The compound represented by the following formula according to the above [2]:

[Chem.12]

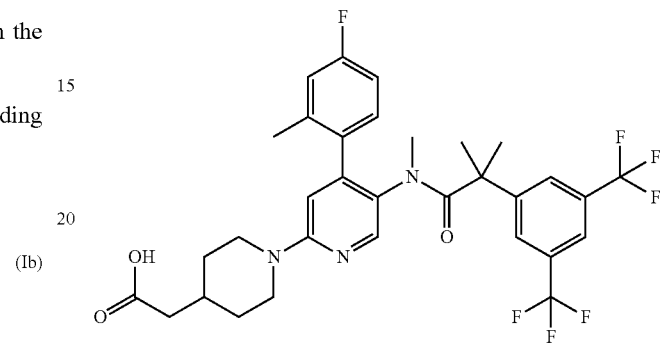

or a pharmaceutically acceptable salt thereof.
[7] The compound represented by the following formula according to the above [2]:

[Chem. 13]

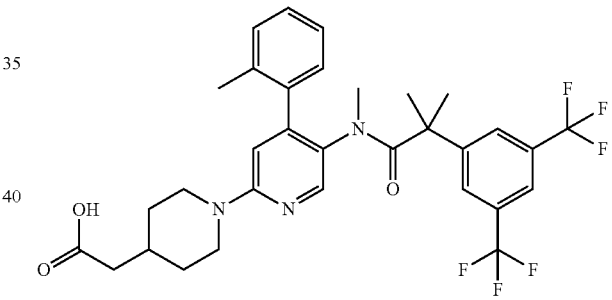

or a pharmaceutically acceptable salt thereof.
[8] The compound represented by the following formula according to the above [2]:

[Chem. 14]

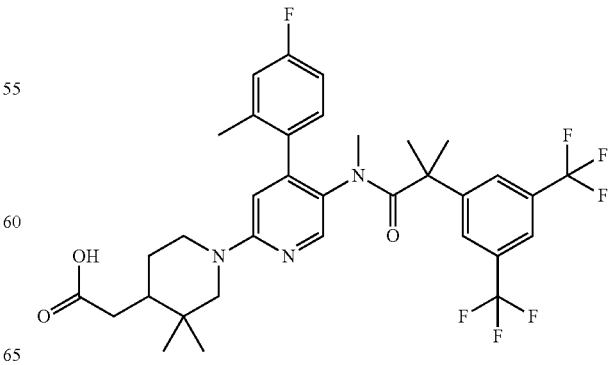

or a pharmaceutically acceptable salt thereof.

[9] The compound represented by the following formula according to the above [2]:

[Chem.15]

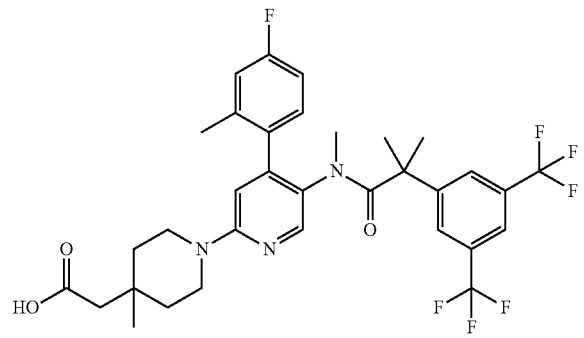

or a pharmaceutically acceptable salt thereof.

[10] The compound represented by the following formula according to the above [1]:

[Chem. 16]

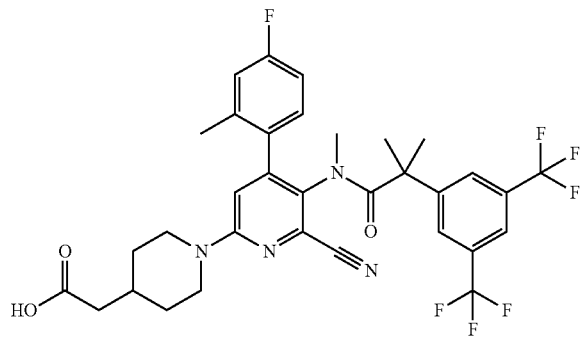

or a pharmaceutically acceptable salt thereof.

[11] A pharmaceutical composition comprising as an active ingredient a compound according to any one of the above [1] to [10], or a pharmaceutically acceptable salt thereof.

[12] The pharmaceutical composition according to the above [11], for use in the prevention or treatment of cancer-chemotherapy-induced nausea and vomiting.

Effect Of The Invention

The compounds of the present invention have an excellent $NK_1$ receptor antagonist activity. And, CYP3A4 inhibitory of the compounds of the present invention is reduced compared to aprepitant. Furthermore, the preferable compounds of the present invention excel in central transportation property and long-acting medicinal effect.

Therefore, the compounds of the present invention or pharmaceutically acceptable salts thereof are usefull as an agent for the prevention or treatment of cancer-chemotherapy-induced nausea and vomiting.

BRIEF DESCRIPTION OF THE DRAWINGS

FIG. 1 shows the effect on cisplatin-induced acute and delayed emetic response. In the figure, each bar chart shows a value of control group (Control), the group intravenously administered with 3 mg/kg of the compound of Example 1 (Ex. No 1, 3 mg kg iv) and the group orally administered with 1 mg/kg of the compound of Example 1 (Ex. No 1, 1 mg/kg, po) in the acute phase, and a value of control group, the group intravenously administered with 3 mg/kg of the compound of Example 1 (Ex. No 1, 3 mg/kg, iv) and the group orally administered with 1 mg/kg of the compound of Example 1 (Ex. No 1, 1 mg/kg, po) in the delayed phase from the left respectively. The vertical axes show the number of retching and vomiting (Retches+Vomites) (the mean+standard error of 5 examples of control group, the mean+standard error of 5 examples of the group intravenously administered, and the mean+standard error of 5 examples of the group orally administered).

MODE FOR CARRYING OUT THE INVENTION

In the present invention, each term has the following meaning unless otherwise specified.

The term "$C_{1-6}$ alkyl" means a straight-chained or a branched alkyl group having 1 to 6 carbon atoms, and for example, methyl, ethyl, propyl, isopropyl, butyl, isobutyl, sec-butyl, tert-butyl can be illustrated.

The term "$C_{1-6}$ alkoxy" means a straight-chained or a branched alkoxy group having 1 to 6 carbon atoms, and for example, methoxy, ethoxy, propoxy, isopropoxy can be illustrated.

In the compounds represented by the formula (I) of the present invention, the symbol "$R_1$" means a substituent of the piperidine ring.

The present invention is further illustrated below.

In the case where the compounds represented by the formula (I) of the present invention contain one or more asymmetric carbon atoms, all stereoisomers in the R- or S-configuration at each of asymmetric carbons and their mixtures are included in the present invention. In such cases, racemic compounds, racemic mixtures, individual enantiomers and mixtures of diastereomers are included in the scope of the present invention. In the case where the compounds represented by the formula (I) of the present invention have the cis-trans isomers, all cis-trans isomers are included in the present invention.

In the present invention, stereochemical determination can be also determined according to well-known methods in the art. For example, see also "Tokuron NMR rittai kagaku", Kodansha, 2012, p. 59.

A compound represented by the formula (I) of the present invention can be converted into pharmaceutically acceptable salts thereof according to a general method. As such salts, acid additive salts and salts with a base can be illustrated.

As the acid additive salt, an acid additive salt with a mineral acid such as hydrochloric acid, hydrobromic acid, hydroiodic acid, sulfuric acid, nitric acid, phosphoric acid and the like, and an acid additive salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like can be illustrated.

As the salt with a base, a salt formed with inorganic base such as a lithium salt, a sodium salt, a potassium salt, a calcium salt, a magnesium salt and the like, and a salt formed with organic base such as N-methyl-D-glucamine, N,N'-dibenzylethylenediamine, triethylamine, piperidine, morpholine, pyrrolidine, arginine, lysine, choline and the like.

In the present invention, a pharmaceutically acceptable salt also includes a solvate thereof with a pharmaceutically acceptable solvent such as water, ethanol or the like.

In an embodiment of a compound represented by the formula (I) of the present invention, n is 0, 1 or 2.

A compound represented by the formula (I) of the present invention can be also prepared, for example, by a method described below or a similar method thereto, or a method described in literatures or a similar method thereto.

Scheme 1

[Chem.17]

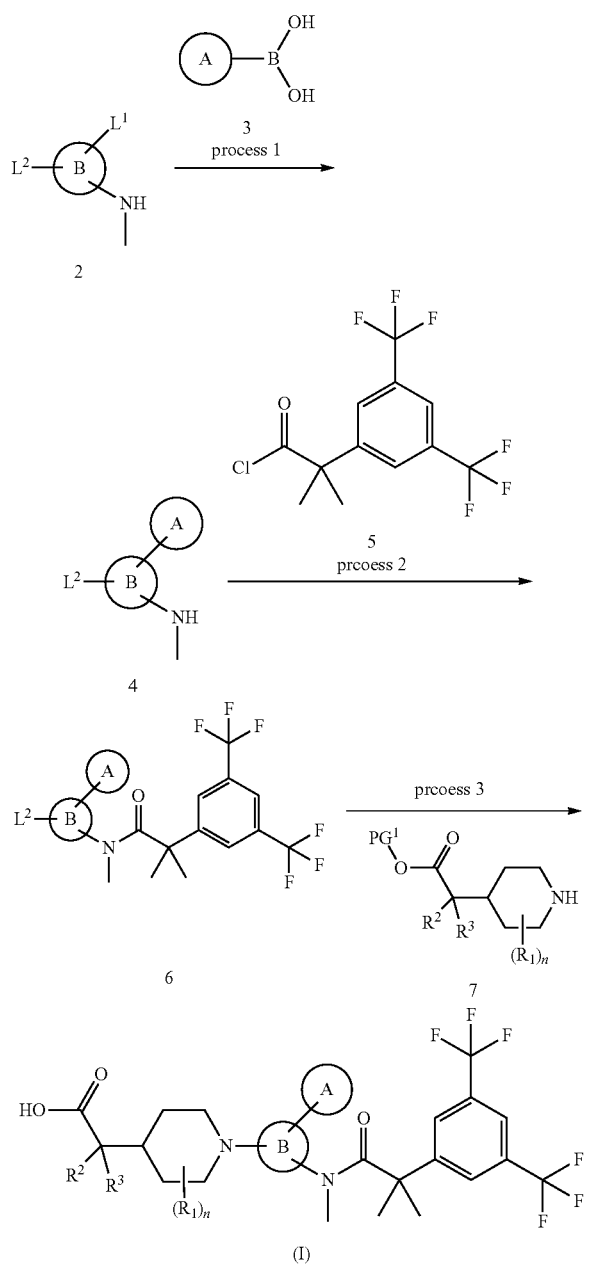

In the formula, $L^1$ and $L^2$ are each independently a leaving group such as a chlorine atom, a bromine atom, an iodine atom, a trifluoromethanesulfonyloxy group or the like. $PG^1$ is a protective group, and ring A, ring B, $R_1$, $R_2$, $R_3$ and n have the same meanings as defined above.

Process 1

Compound (4) can be also prepared by conducting coupling reaction of Compound (2) with Compound (3) in an inert solvent in the presence of a base and a palladium catalyst.

Process 2

Compound (6) can be also prepared by conducting condensation reaction of Compound (4) with Compound (10) in an inert solvent in the presence of a base.

Process 3

Compound (I) can be also prepared by allowing Compound (6) to react with Compound (7), and conducting deprotection in an inert solvent in the presence or absence of a base.

As the inert solvent, for example, N,N-dimethylformamide, N-methylpyrrolidone, dimethylsulfoxide, diethyl ether, tetrahydrofuran, 1, 4-dioxane, 1,2-dimethoxyethane, benzene, toluene, xylene, and a mixed solvent thereof can be illustrated. As the base, potassium carbonate, sodium carbonate, cesium carbonate, sodium hydroxide, potassium hydroxide, lithium hydroxide, potassium fluoride, cesium fluoride, triethylamine, pyridine, N,N-diisopropylethylamine, 2,6-lutidine, and 1,8-diazabicyclo[5,4,0]-7-undecene can be illustrated. The reaction temperature is usually at 0° C. to reflux temperature. The reaction time is usually from 30 minutes to 7 days, varying based on a used starting material, solvent and reaction temperature or the like. The above reaction can also be conducted by using a microwave reactor (Biotage). When a microwave reactor is used, the reaction is conducted at pressure range: 1 to 30 bar, power range: 1 to 400 W, reaction temperature: room temperature to 300° C., and reaction time: a minute to 1 day, varying based on a used starting material, solvent and model.

Scheme 2

[Chem.18]

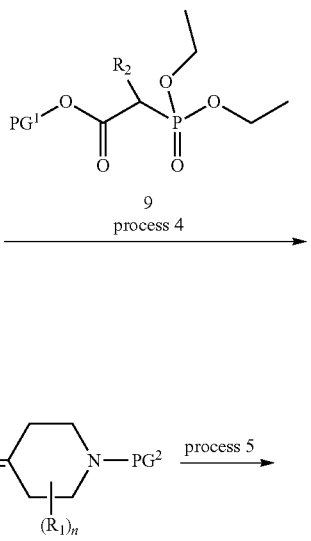

-continued

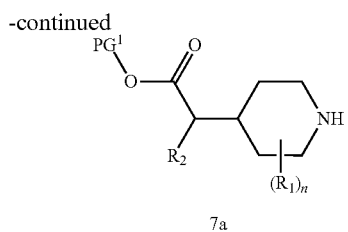

7a

In the formula, PG¹ and PG² represent a protective group, and $R_1$, $R_2$, and n have the same meanings as defined above.

Process 4

Compound (10) can also be prepared by conducting olefination reaction of Compound (9) with Compound (8) in an inert solvent in the presence of a base. As the inert solvent, for example, N,N-dimethylformamide, N-methylpyrrolidone, dimethylsulfoxide, diethyl ether, tetrahydrofuran, 1,4-dioxane, 1,2-dimethoxyethane, benzene, toluene, xylene, and a mixed solvent thereof can be illustrated. As the base, sodium hydride, sodium methoxide, potassium carbonate, cesium carbonate, potassium tert-butoxide, triethylamine, N,N-diisopropylethylamine, and 1,8-diazabicyclo[5,4,0]-7-undecene can be illustrated. The reaction temperature is usually at −78° C. to reflux temperature. The reaction time is usually from 30 minutes to 7 days, varying based on a used starting material, solvent and reaction temperature or the like. The reaction can also be conducted by using a microwave reactor (Biotage).

Process 5

Compound (7a) can also be also prepared by conducting olefin reduction such as catalytic reduction method of Compound (10) and so on, and conducting deprotection. The catalytic reduction method can be conducted, for example, by allowing Compound (10) to react by using a catalyst under a hydrogen atmosphere in a solvent. As the solvent, for example, methanol, ethanol, ethyl acetate, tetrahydrofuran acetic acid and the like can be illustrated. As the catalyst, for example, palladium-carbon powder, rhodium-carbon powder, platinum-carbon powder, platinum-carbon powder doped with vanadium can be illustrated. The reaction temperature is usually at room temperature to reflux temperature. The reaction time is usually from 30 minutes to 7 days, varying based on a used starting material, solvent and reaction temperature or the like.

The above-mentioned schemes are exemplary for preparing compounds represented by the formula (I) of the present invention and synthetic intermediates thereof. The above schemes can be changed or modified into schemes which a person ordinarily skilled in the art can easily understand.

In the above schemes, when a protective group is necessary based on variation of functional group, operations of introduction and deprotection can also be conducted optionally in combination according to a general method.

Compounds represented by the formula (I) of the present invention and intermediates thereof can also be isolated and purified, if required, according to conventional isolation and purification techniques well known to a person ordinarily skilled in the art in the relevant field, such as solvent extraction, crystallization, recrystallization, chromatography, preparative high performance liquid chromatography or the like.

The compounds of the present invention have an excellent $NK_1$ receptor antagonist activity, and thus can also be used as an agent for the prevention or treatment of various diseases mediated by $NK_1$ receptor. For example, the compounds of the present invention are useful as antiemetic agent, especially useful as preventive agent of cancer-chemotherapy (for example, cisplatin)-induced gastrointestinal symptom (for example, nausea and vomiting). Preferable compounds of the present invention are not only useful for acute cancer-chemotherapy-induced nausea and vomiting but also delayed cancer-chemotherapy-induced nausea and vomiting.

In an embodiment, the compounds of the present invention have an excellent $NK_1$ receptor antagonist activity, and thus can also be used as an agent for the prevention of postoperative nausea and vomiting (PONV), nausea and vomiting associated with radiotherapy, morphine-induced vomiting or motion sickness, and the treatment of schizophrenia, social phobia, anxiety and depression, alcoholism, irritable bowel syndrome, ulcerative colitis, coughing, asthma, atopic dermatitis, psoriasis, pruritus, pain, migraine, tinintus, benign prostatic hyperplasia, overactive bladder or urinary incontinence.

Pharmaceutical compositions of the present invention can be administered in various dosage forms depending on their usages. As such dosage forms, for example, powders, granules, fine granules, dry syrups, tablets, capsules, injections, liquids, ointments, suppositories and poultices can be illustrated, which are administered orally or parenterally.

Pharmaceutical compositions of the present invention can be prepared by using a compound represented by the formula (I) or a pharmaceutically acceptable salt thereof and at least one of a pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

When a pharmaceutical composition of the present invention is used in the prevention or treatment, the dosage of a compound represented by the formula (I) or a pharmaceutically acceptable salt thereof as the active ingredient is appropriately decided to depend on the age, sex, body weight, degree of disorders and treatment of each patient and the like. The dosage for an adult can be decided within the range of, for example, 1 to 1000 mg per day, 0.1 to 500 mg per day, 0.1 to 100 mg per day, or 0.1 to 50 mg per day in the case of oral administration, and the daily dose can be divided into one, two, three or four times per day and adininistered. And the dosage for an adult can be decided within the range of, for example, 1 to 1000 mg per day, 0.1 to 500 mg per day, 0.1 to 100 mg per day, or 0.1 to 50 mg per day in the case of parenteral administration, and the daily dose can be divided into one, two, three or four times per day and administered.

When a pharmaceutical composition of the present invention is used in the prevention of cancer-chemotherapy-induced nausea and vomiting, this pharmaceutical can also be administered before administration of antineoplastic agents. For example, the pharmaceutical can be administered immediately before administration to before an hour and a half of the administration in chemotherapy, and after the second day, the pharmaceutical can also be administered in the morning.

In an embodiment, a compound represented by the formula (I) of the present invention or a pharmaceutically acceptable salt thereof can also be used in combination with any other medicament other than $NK_1$ receptor antagonists. As such other medicaments used in combination, for example, corticosteroid and 5-HT$_3$ receptor antagonist antiemetic agent can be illustrated.

When a compound represented by the formula (I) of the present invention or a pharmaceutically acceptable salt thereof are used in combination with the other medicament, it can be administered as a formulation comprising together with there active ingredients or as formulations each of which is separately formulated from each active ingredient. When separately formulated, these formulations can be administered separately or concurrently.

Furthermore, the dosage of the compound represented by the formula (I) of the present invention can be reduced depending on the dosage of the other medicaments used in combination.

EXAMPLES

The present invention is further illustrated in more detail by way of the following Reference Examples, Examples and Test Examples. However, the present invention is not limited thereto.

Reference Example 1

(3-Methylpiperidin-4-yl)acetic acid ethyl ester

To a suspension of sodium hydride (60%, 0.17 g) in tetrahydrofuran (5 mL) was added triethyl phosphonoacetate (1.04 g) under ice-cooling, and the mixture was stirred at room temperature for 1 hour. To the reaction mixture was added a solution of 3-methyl-4-oxopiperidine-1-carboxylic acid tert-butyl ester (0.50 g) in tetrahydrofuran (5 mL) at room temperature, and the mixture was stirred at 50° C. for 2.5 hours. The reaction mixture was cooled to mom temperature and water was added. The resulting mixture was extracted with ethyl acetate. The organic layer was washed with water and brine, and dried over anhydrous magnesium sulfate, and the solvent was removed under reduced pressure. The obtained residue was purified by column chromatography on silica gel (eluent: n-hexane/ethyl acetate) to give 4-ethoxycarbonylmethylene-3-methylpiperidine-1-carboxylic acid tert-butyl ester (0.65 g). To a solution of the obtained compound (0.65 g) in ethanol (12 mL) was added 10% palladium on carbon (250 mg, wet) at room temperature, and the mixture was stirred at room temperature under a hydrogen gas atmosphere for 18 hours. The reaction mixture was diluted with ethyl acetate and the resulting mixture was stirred at room temperature for 15 minutes. The reaction mixture was filtered through a Celite pad, and the filtrate was concentrated under reduced pressure to give 4-ethoxycarbonylmethyl-3-methylpiperidine-1-carboxylic acid tert-butyl ester (0.64 g). To a solution of the obtained compound (0.64 g) in ethyl acetate (10 mL) was added 4 mol/L hydrochloric, acid (ethyl acetate solution, 10 mL) at room temperature, and the mixture was stirred at room temperature for 39 hours. The reaction mixture was concentrated under reduced pressure, and to the residue was added a saturated aqueous sodium hydrogen carbonate solution. The resulting mixture was extracted with a mixed solvent of dichloromethane-isopropyl alcohol (dichloromethane/isopropyl alcohol=3/1) twice. The combined organic layer was dried over anhydrous sodium sulfate, and the solvent was removed under reduced pressure to give the title compound (0.39 g).

Reference Examples 2 and 3

The compounds of Reference Examples 2 to 3 were prepared in a similar manner to that described in Reference Example 1 using the corresponding starting materials.

Reference Example 4

(6-Chloro-4-iodopyridin-3-yl)cathamic acid tert-butyl ester

To a solution of (6-chloropyridin-3-yl)cathamic acid tert-butyl ester (5.0 g) and N,N,N',N-tetramethylethane-1,2-diamine (7.7 g) in diethyl ether (120 mL) was added dropwise n-buthyllithium (2.65 mol/L n-hexane solution, 25 mL) at −78° C. under an argon gas atmosphere. After the mixture was stirred at −10° C. for 2 hours, a solution of iodine (11.4 g) in diethyl ether (40 mL) was added dropwise at −78° C. The resulting mixture was stirred at room temperature for 1 day. To the reaction mixture was added a saturated aqueous ammonium chloride solution, and the resulting mixture was extracted with diethyl ether. The organic layer was washed with 10% aqueous sodium pyrosulfite and brine, and dried over anhydrous magnesium sulfate, and the solvent was removed under reduced pressure. The obtained crude product was purified by column chromatography on silica gel (eluent: n-hexane/ethyl acetate) to give the title compound (2.59 g).

Reference Example 5

(6-Chloro-4-iodopyridin-3-yl)methylcarbamic acid tert-butyl ester

To a solution of (6-Chloro-4-iodopyridin-3-yl)carbamic acid tert-butyl ester (2.59 g) in N,N-dimethylformamide (30 mL) was added sodium hydride (60%, 0.32 g) under ice-cooling, and the mixture was stifled at room temperature for 30 minutes. To the mixture was added iodomethane (2.60 g) under ice-cooling and the mixture was stirred at room temperature overnight. To the reaction mixture was added a saturated aqueous sodium hydrogen carbonate solution, and the resulting mixture was extracted with ethyl acetate. The organic layer was washed with water and brine, and dried over anhydrous magnesium sulfate, and the solvent was removed under reduced pressure. The obtained crude product was purified by column chromatography on aminopropylated silica gel (eluent: n-hexane/ethyl acetate) to give the title compound (2.66 g).

Reference Example 6

(6-Chloro-4-iodopyridin-3-yl)methylamine

To a solution of (6-Chloro-4-iodopyridin-3-yl)methylcarbamic acid tert-butyl ester (2.66 g) in dichloromethane (10 mL) was added trifluoroacetic acid (8.23 g) under ice-cooling, and the mixture was stirred at room temperature for 2 hours. The reaction mixture was concentrated under reduced pressure, and to the residue was added a saturated aqueous sodium carbonate solution, and the mixture was extracted with ethyl acetate. The organic layer was washed with water and brine, and dried over anhydrous magnesium sulfate, and the solvent was removed under reduced pressure to give the title compound (1.89 g).

Reference Example 7

[6-Chloro-4-(4-fluoro-2-methylphenyl]pyridin-3-yl)
methylamine

To a mixed solution of (6-Chloro-4-iodopyridin-3-yl)
methylamine (1.89 g) and 4-fluoro-2-methylphenyl boronic
acid (1.30 g) in 1,2-dimethoxyethane (20 mL)-water (20
mL) were added palladium (II) acetate (0.16 g), triphenylphosphine (0.37 g) and sodium carbonate (3.73 g) at room
temperature, and the mixture was stirred at 90° C. overnight.
The reaction mixture was cooled to room temperature and
water was added. The resulting mixture was extracted with
ethyl acetate. The organic layer was washed with water and
brine, and dried over anhydrous magnesium sulfate, and the
solvent was removed under reduced pressure. The obtained
crude product was purified by column chromatography on
aminopropylated silica gel (eluent: n-hexane/ethyl acetate)
to give the title compound (1.56 g).

Reference Example 8

(6-Chloro-4-ortho-tolylpyridin-3-yl)methylamine

To a mixed solution of (6-Chloro-4-iodopridin-3-y)methylamine (0.70 g) and 2-methylphenyl boronic acid (0.42 g)
in 1,2-dimethoxyethane (10 mL)-water (10 mL) were added
palladium (II) acetate (0.058 g), triphenylphosphine (0.14 g)
and sodium carbonate (1.38 g) at room temperature, and the
mixture was stirred at 90° C. overnight. The reaction mixture
was cooled to room temperature and water was added. The
resulting mixture was extracted with ethyl acetate. The
organic layer was washed with water and brine, and dried
over anhydrous magnesium sulfate, and the solvent was
removed under reduced pressure. The obtained crude product was purified by column chromatography on silica gel
(eluent: n-hexane/ethyl acetate) to give the title compound
(0.54 g).

Reference Example 9

2-(3,5-Bistrifluoromethylphenyl)-N-[6-chloro-4-(4-fluoro-2-methylphenyl)pyridin-3-yl]-N-methylisobutylamide To a solution of 2-(3,5-bistrifluoromethylphenyl)-2-methylpropionic acid (0.66 g) in dichloromethane (10 mL) was
added oxalyl chloride (0.56 g) and N,N-dimethylformamide
(2 drops) at room temperature, and the mixture was stirred
at the same temperature for 1 hour. The reaction mixture was
concentrated under reduced pressure to give the residue.
Under an argon gas atmosphere, to a solution of [6-Chloro-4-(4-fluoro-2-methylphenyl)pyridin-3-yl]methylamine
(0.50 g) in tetrahydrofuran (10 mL) was added potassium
bis(trimethylsilyl)amide (0.500 mol/L toluene solution, 5.0
mL) under ice-cooling, and the mixture was stirred at room
temperature for 30 minutes. To the reaction mixture was
added dropwise a solution of the above residue in tetrahydrofuran (5 mL) under ice-cooling, and the mixture was
stirred at room temperature for 2 hours. To the reaction
mixture was added 1.0 mol/L aqueous sodium hydrogen
carbonate solution, and the mixture was extracted with ethyl
acetate. The organic layer was washed with water and brine,
and dried over anhydrous magnesium sulfate, and the solvent was removed under reduced pressure. The obtained
crude product was purified by column chromatography on
aminopropylated silica gel (eluent: n-hexane/ethyl acetate)
to give the title compound (1.03 g).

Reference Example 10

2-(3,5-Bistrifluoromethylphenyl)-N-(6-chloro-4-ortho-tolylpyridin-3-yl)-N-methylisobutylamide To a solution of 2-(3,5-bistrifluoromethylphenyl)-2-methylpropionic acid (0.77 g) in dichloromethane (12 mL) was
added oxalyl chloride (0.65 g and N,N-dimethylformamide
(2 drops) at room temperature, and the mixture was stirred
at the same temperature for 1 hour. The reaction mixture was
concentrated under reduced pressure to give the residue.
Under an argon gas atmosphere, to a solution of (6-Chloro-4-ortho-tolylpyridin-3-yl)methylamine (0.54 g) in tetrahydrofuran (12 mL) was added potassium bis(trimethylsilyl)
amide (0.500 mol/L toluene solution, 6.0 mL) under ice-cooling, and the mixture was stirred at room temperature for
30 minutes. To the reaction mixture was added dropwise a
solution of the above residue in tetrahydrofuran (6 mL)
under ice-cooling, and the mixture was stirred at room
temperature for 1 hours. To the reaction mixture was added
1.0 mol/L aqueous sodium hydrogen carbonate solution, and
the mixture was extracted with ethyl acetate. The organic
layer was washed with water and brine, and dried over
anhydrous magnesium sulfate, and the solvent was removed
under reduced pressure. The obtained crude product was
purified by column chromatography on aminopropylated
silica gel (eluent: n-hexane/ethyl acetate) to give the title
compound (1.0 g).

Reference Example 11

[5'-{[2-(3,5-Bistrifluoromethylphenyl)-2-methylpropionyl]methylamino}-4'-(4-fluoro-2-methylphenyl)-3,4,5,6-tetrahydro-2H-[1,2']bipyridinyl-4-yl]acetic
acid ethyl ester A suspension of 2-(3,5-bistrifluoromethylphenyl)-N-[6-chloro-4-(4-fluoro-2-methylphenyl)pyridin-3-yl]-N-methylisobutylamide (0.79 g), (piperidin-4-yl)acetic acid ethyl
ester (0.38 g), and potassium carbonate (0.41 g) in dimethyl
sulfoxide (4.5 mL) was stirred at 180° C. under microwave
irradiation for 1 hour. The reaction mixture was cooled to
room temperature and water was added. The resulting mixture was extracted with ethyl acetate. The organic layer was
washed with water and brine, and dried over anhydrous
magnesium sulfate, and the solvent was removed under
reduced pressure. The obtained crude product was purified
by column chromatography on aminopropylated silica gel
(eluent: n-hexan/ethyl acetate=100/0-60/40). The obtained
material was purified by column chromatography on silica
gel (eluent: n-hexane/ethyl acetate=100/0-60/40) to give the
title compound (0.38 g).

Reference Example 12

(5'-{[2-(3,5-Bistrifluoromethylphenyl)-2-methylpropionyl]methylamino}-4'-ortho-tolyl-3,4,5,6-tetrahydro-2H-[1,2']bipyridinyl-4-yl)acetic acid ethyl
ester A suspension of 2-(3,5-bistrifluoromethylphenyl)-N-(6-chloro-4-ortho-tolylpyridin-3-yl)-N-methylisobutylamide
(0.50 g), (piperidin-4-yl)acetic acid ethyl ester (0.25 g), and
potassium carbonate (0.27 g) in dimethyl sulfoxide (3.0 mL)

17 was stirred at 180° C. under microwave irradiation for 2 hours. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-50/50) to give the title compound (0.35 g).

Reference Example 13

5'-{[2-(3,5-Bistrifluoromethylphenyl)-2-methylpropionyl]methylamino}-4'-(4-fluoro-2-methyl phenyl)-3,3-dimethyl-3,4,5,6-tetrahydro-2H-[1,2']bipyridinyl-4-yl]acetic acid ethyl ester A solution of 2-(3,5-bistrifluoromethylphenyl)-N-[6-chloro-4-(4-fluoro-2-methylphenyl)pyridin-3-yl]-N-methylisobutylamide (0.05 g) and (3,3-dimethylpiperidin-4-yl)acetic acid ethyl ester (0.094 g) in 1-methyl-2-pyrrolidone (0.5 mL) was stirred at 180° C. under microwave irradiation for 3 hours. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexan/ethyl acetate=100/0-50/50) to give the title compound (0.043 g).

Reference Example 14

5'-{[2-(3,5-Bistrifluoromethylphenyl)-2-methylpropionyl]methylamino}-4'-(4-fluoro-2-methyl phenyl)-3-methyl-3,4,5,6-tetrahydro-2H-[1,2']bipyridinyl-4-yl]acetic acid ethyl ester A solution of 2-(3,5-bistrifluoromethylphenyl)-N-[6-chloro-4-(4-fluoro-2-methylphenyl)pyridin-3-yl]-N-methylisobutylamide (0.05 g) and (3-methylpiperidin-4-yl)acetic acid ethyl ester (0.087 g) in 1-methyl-2-pyrrolidone (0.5 mL) was stirred at 180° C. under microwave irradiation for 1 hour. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=100/0-50/50) to give the title compound (0.040 g).

Reference Example 15

[5'-{[2-(3,5-Bistrifluoromethylphenyl)-2-methylpropionyl]methylamino}-4'-(4-fluoro-2-methyl phenyl)-3-methoxyl-3,4,5,6-tetrahydro-2H-[1,2']bipyridinyl-4-yl]acetic acid ethyl ester A solution of 2-(3,5-bistrifluoromethylphenyl)-N-[6-chloro-4-(4-fluoro-2-methylphenyl)pyridin-3-yl]-N-methylisobutylamide (0.05 g) and (3-methoxypiperidin-4-yl)acetic acid ethyl ester (0.094 g) in 1-methyl-2-pyrrolidone (0.5 mL) was stirred at 180° C. under microwave irradiation for 1 hour. The reaction mixture was cooled to room temperature and water was added. The resulting ,mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=100/0-60/40) to give the title compound (0.025 g).

Reference Example 16

2-Methyl-2-piperidin-4-ylpropionic acid ethyl ester

To a solution of lithium diisopropylamide (1.09 mol/L tetrahydrofuran/n-hexane solution, 30.0 mL) in tetrahydrofuran (40 mL) was added dropwise a solution of ethyl isobutylate in tetrahydrofuran (20 mL) at −78° C. under an argon gas atmosphere, and the mixture was stirred at the same temperature for 1 hour. To the reaction mixture was added a solution of 4-oxopiperidine-1-carboxylic acid benzyl ester (5.83 g) in tetrahydrofuran (50 mL) at −78° C., and the mixture was stirred at room temperature overnight. To the reaction mixture was added a saturated aqueous ammonium chloride solution, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-10/90) to give 4-(1-ethoxycarbonyl-1-methylethyl)-4-hydroxypiperidine-1-carboxylic acid benzyl ester (6.13 g), To a solution of the obtained compound (6.13 g) in toluene (100 mL) was added (methoxycarbonylsulfamoyl) triethylammonium hydroxide inner salt (5.00 g) at room temperature, and the mixture was stirred at 90° C. for 2 hours. The reaction mixture was cooled to room temperature and water was added. The resulting mixture was extracted with ethyl acetate. The organic layer was washed with saturated aqueous sodium hydrogen carbonate solution, water and brine, and dried over anhydrous magnesium sulfate, and the solvent was removed under reduced pressure. The obtained crude product was purified by column chromatography on silica gel (eluent: n-hexane/ethyl acetate=100/0-50/50) to give 4-(1-ethoxycarbonyl-1-methylethyl)-3,6-dihydro-2H-pyridine-1-carboxylic acid benzyl ester (5.85 g). Under a hydrogen gas atmosphere, a mixture of the obtained compound (5.85 g) and Pearlman's catalyst (0.600 g) in methanol (65 mL) and ethyl acetate (65 mL) was stirred at room temperature overnight. The reaction mixture was filtered through a Celite pad, and the filtrate was concentrated under reduced pressure to give the title compound (3.18 g).

Reference Example 17

2-Piperidin-4-ylpropionic acid ethyl ester

To a suspension of sodium hydride (60%, 0.78 g) in N,N-dimethylformamide (20 mL) was added 2-(diethoxyphosphoryl)propionic acid ethyl ester (4.44 g) under ice-cooling, and the mixture was stirred at the same temperature for 30 minutes. To the reaction mixture was added a solution of 4-oxopiperidine-1-carboxylic acid benzyl ester (3.50 g) in N,N-dimethylformamide (10 mL) under ice-cooling, and the mixture was stirred at room temperature for 1 hour. To the reaction mixture was added water, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-50/50) to give 4-(1-ethoxycarbonylethylidene)piperidine-1-carboxylic acid benzyl ester (4.60 g). Under a hydrogen gas atmosphere, a mixture of the obtained compound (4.60 g) and 10% palladium on carbon (500 mg, wet in methanol (50 mL) was stirred at room temperature for 2 hours. The reaction mixture was filtered through a Celite pad, and the filtrate was concentrated under reduced pressure to give the title compound (2.85 g).

Reference Example 18

(4-Methylpiperidin-4-yl)acetic acid ethyl ester

To a solution of 4-hydroxymethyl-4-methyl piperidine-1-carboxylic acid tert-butyl ester (0.67 g) and triethylamine (0.44 g) in dichloromethane (15 mL) was added methanesulfonyl chloride (0.40 g) at room temperature, and the mixture was stirred at the same temperature for 3 hours. The reaction mixture was washed with water and brine, and dried over anhydrous magnesium sulfate. The solvent was removed under reduced pressure to give 4-methanesulfonyloxymethyl-4-methylpiperidine-1-carboxylic acid tert-butyl ester (0.85 g). To a solution of the obtained compound (0.85 g) in N,N-dimethylformamide (6 mL) was added sodium cyanide (0.27 g) at room temperature, and the mixture was stirred at 50° C. for 5 hours and at 80° C. for 13 hours. To the reaction mixture were added sodium cyanide (0.22 g) and sodium iodide (0.02 g), and the mixture was stirred at 120° C. for 8 hours. To the reaction mixture was added sodium cyanide (0.72 g), and the mixture was stirred at 140° C. for 17 hours. The reaction mixture was cooled to room temperature and water was added. The resulting mixture was extracted with a mixed solvent of n-hexane and ethyl acetate (n-hexane/ethyl acetate=1/4). The organic layer was washed with water and brine, and dried over anhydrous magnesium sulfate, and the solvent was removed under reduced pressure. The obtained crude product was purified by column chromatography on silica gel (eluent: n-hexane/ethyl acetate=80/20-50/50) to give 4-cyanomethyl-4-methylpiperidine-1-carboxylic acid tert-butyl ester (0.53 g). A mixture of the obtained compound (0.53 g) and concentrated hydrochloric acid (12 mL) was stirred at 110° C. for 47 hours. The reaction mixture was cooled to room temperature, and to the mixture were added water (24 mL), aqueous sodium hydroxide solution (2.0 mol/L, 45 mL) and di-tert-butyl dicarbonate (0.51 g), and the resulting mixture was stirred at room temperature for 21 hours. The solvent was removed under reduced pressure, and to the residue were added water and hydrochloric acid (2.0 mol/L, 3 mL), and the resulting mixture was extracted with ethyl acetate. The organic layer was dried over anhydrous sodium sulfate, and the solvent was removed under reduced pressure to give 4-carboxymethyl-4-methylpiperidine-1-carboxylic acid tert-butyl ester (0.34 g). To a solution of the obtained compound (0.34 g) in N,N-dimethylformamide (5 mL) were added potassium carbonate (0.27 g) ethyl iodide (0.41 g) at room temperature, and the resulting mixture was stirred at the same temperature for 22 hours. To the reaction mixture was added water, and the resulting mixture was extracted with diethyl ether. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-60/40) to give 4-ethoxycarbonylmethyl-4-methylpiperidine-1-carboxylic acid tert-butyl ester (0.28 g). To a solution of the obtained compound (0.28 g) in 1,4-dioxane (5 mL) was added hydrogen chloride (4.0 mol/L 1,4-dioxane solution, 5.0 mL) at room temperature, and the mixture was stirred at the same temperature for 26 hours. The solvent was removed under reduced pressure, and to the residue was added saturated aqueous sodium hydrogen carbonate, and the resulting mixture was extracted with a mixed solvent of dichloromethane/isopropyl alcohol (dichloromethane/isopropyl alcohol=3/1) twice. The combined organic layer was dried over anhydrous sodium sulfate, and the solvent was removed under reduced pressure to give the title compound (0.17 g).

Reference Example 19

6-Chloro-3-nitropyridine-2-carbonitrile

To a solution of 2, 6-dichloro-3-nitropyridine (2.50 g) in N-methylpyrrolidone (25 mL) was added copper (I) cyanide (2.32 g) at room temperature, and the mixture was stirred at 180° C. for 1 hour. The reaction mixture was cooled to room temperature, and to the mixture were added ethyl acetate and water. The mixture was filtered through a Celite pad. The filtrate was washed with brine, and the separated aqueous layer was re-extracted with ethyl acetate. The combined organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-70/30) to give the title compound (0.90 g).

Reference Example 20

3-Amino-6-chloropyridine-2-carbonitrile

To a solution of 6-chloro-3-nitropyridine-2-carbonitrile (0.32 g and concentrated hydrochloric acid (1.2 mL) in ethanol (3.6 mL) was added iron powder (0.34 g) at room temperature, and the mixture was heated at reflux for 30 minutes. The reaction mixture was cooled to room temperature, and basified by addition of saturated aqueous sodium hydrogen carbonate solution. To the mixture was added ethyl acetate, and the resulting mixture was filtered through a Celite pad, and the filtrate was extracted with ethyl acetate. The organic layer was washed with water and brine, dried over anhydrous magnesium sulfate. The solvent was removed under reduced pressure to give the title compound (0.24 g).

Reference Example 21

3-Amino-4-bromo-6-chloropyridine-2-carbonitrile

To a solution of 3-amino-6-chloropyridine-2-carbonitrile (0.24 g) in N,N-dimethylformamide (8 mL) was added N-bromosuccinimide (0.37 g) at room temperature, and the mixture was stirred at the same temperature overnight. To the reaction mixture was added saturated aqueous sodium thiosulfate solution, and the resulting mixture was extracted with ethyl acetate. The organic layer was washed with brine, and dried over anhydrous magnesium sulfate, and the solvent was removed under reduced pressure. The obtained crude product was purified by column chromatography on aminopropylated silica gel (eluent: n-hexane/ethyl acetate=75/25-50/50) to give the title compound (0.30 g).

Reference Example 22

3-Amino-6-chloro-4-(4-fluoro-2-methylphenyl)pyridine-2-carbonitrile

A mixture of 3-amino-4-bromo-6-chloropyridine-2-carbonitrile (0.15 g), 4-fluoro-2-methylphenylboronic acid (0.08 g), tetrakis(triphenylphosphine)palladium(0) (0.07 g), sodium carbonate (0.20 g), 1,2-dimethoxyethane (3.2 mL) and water (0.8 mL) was stirred at 100° C. under microwave irradiation for 1 hour. The reaction mixture was cooled to room temperature and water was added. The resulting mixture was extracted with ethyl acetate. The organic layer was washed with saturated aqueous sodium hydrogen carbonate solution and brine, and dried over anhydrous magnesium sulfate, and the solvent was removed under reduced pressure. The obtained crude product was purified by column chromatography on aminopropylated silica gel (eluent: n-hexane/ethyl acetate=50/50-0/100) to give the title compound (0.14 g).

Reference Example 23

2-(3,5-Bistrifluoromethylphenyl)-N-[6-chloro-2-cyano-4-(4-fluoro-2-methylphenyl)pyridin-3-yl] isobutylamide To a solution of 2-(3,5-bistrifluoromethylphenyl)-2-methylpropionic acid (0.31 g) in dichloromethane (2.6 mL) were added oxalyl chloride (0.26 g) and N,N-dimethylformamide (2 drops) at room temperature, and the mixture was stirred at the same temperature for 1 hour. The reaction mixture was concentrated under reduced pressure to give the residue. To a solution of 3-amino-6-chloro-4-(4-fluoro-2-methylphenyl) pyridine-2-carbonitrile (0.14 g) in tetrahydrofuran (5 mL) was added sodium bis(trimethylsilyl)amide (1.0 mol/L tetrahydrofuran solution, 1.1 mL) under ice-cooling, and the mixture was stirred at the same temperature for 30 minutes. To the reaction mixture was added dropwise a solution of the above residue in tetrahydrofuran (2.0 mL) under ice-cooling, and the mixture was stirred at room temperature for 30 minutes. To the reaction mixture was added a saturated aqueous sodium hydrogen carbonate solution, and the resulting mixture was extracted with ethyl acetate. The organic layer was washed with water and brine, and dried over anhydrous magnesium sulfate, and the solvent was removed under reduced pressure. The obtained crude product was purified by column chromatography on aminopropylated silica gel (eluent: n-hexane/ethyl acetate=85/15-40/60) to give the title compound (0.21 g).

Reference Example 24

2-(3,5-Bistrifluoromethylphenyl)-N-[6-chloro-2-cyano-4-(4-fluoro-2-methylphenyl)pyridin-3-yl]-N-methylisobutylamide To a solution of 2-(3,5-bistrifluoromethylphenyl)-N[6-chloro-2-cyano-4-(4-fluoro-2-methylphenyl)pyridin-3-yl] isobutylamide (0.21 g) in N,Ndimethylformamide (2.4 mL) was added sodium hydride (60%, 0.018 g) under ice-cooling, and the mixture was stirred at the same temperature for 5 minutes. To the reaction mixture was added iodomethane (0.11 g) under ice-cooling and the mixture was stirred at room temperature overnight. To the reaction mixture was added water, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-50/50) to give the title compound (0.09 g).

Reference Example 25

[5'-{[2-(3,5-Bistrifluoromethylphenyl)-2-methylpropionyl]methylamino}-6'-cyano-4'-(4-fluoro-2-methylphenyl)-3,4,5,6-tetrahydro-2H-[1,2']bipyridinyl-4-yl]acetic acid ethyl ester A suspension of 2-(3,5-bistrifluoromethylphenyl)-N-[6-chloro-2-cyano-4-(4-fluoro-2-methylphenyl)pyridin-3-yl]-N-methylisobutylamide (0.03 g), piperidin-4-yl acetic acid ethyl ester (0.05 g) and potassium carbonate (0.02 g) in dimethyl sulfoxide (1.0 mL was stirred at 1.00° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on aminopropylated silica gel (eluent: n-hexane/ethyl acetate=80/20-20/80) to give the title compound (0.02 g).

Reference Example 26

2-{[5'-[2-(3,5-Bistrifluoromethylphenyl)-2-methylpropionyl]methylamino}-4'-(4-fluoro-2-methylphenyl)-3,4,5,6-tetrahydro-2H-[1,2']bipyridinyl-4-yl]-2-methylpropionic acid ethyl ester A mixture of 2-(3,5-bistrifluoromethylphenyl)-N-[6-chloro-4-(4-fluoro-2-methylphenyl)pyridin-3-yl]-N-methylisobutylamide (0.15 g), 2-methyl-2-piperidin-4-yl propionic acid ethyl ester (0.28 g and N-methylpyrrolidone (1.5 mL) was stirred at 190° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-60/40) to give the title compound (0.14 g).

Reference Example 27

2-[5'-{[2-(3,5-Bistrifluoromethylphenyl)-2-methylpropionyl]methylamino}-4'-(4-fluoro-2-methylphenyl)-3,4,5,6-tetrahydro-2H-[1,2]bipyridinyl-4-yl] propionic acid ethyl ester A suspension of 2-(3,5-bistrifluoromethylphenyl)-N-[6-chloro-4-(4-fluoro-2-methylphenyl)pyridin-3-yl]-N-methylisobutylamide 0.48 g), 2-piperidin-4-yl propionic acid ethyl ester (0.83 g) and potassium carbonate (0.25 g) in N-methylpyrrolidone (3.6 mL) was stirred at 190° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-50/50) to give the title compound (0.51 g).

Reference Examples 28 and 29

N-[4-[(S)-2-((S)-4-Benzyl-2-oxo-oxazolidin-3-yl)-1-methyl-2-oxo-ethyl]-4'-(4-fluoro-2-methylphenyl)-3,4,5,6-tetrahydro-2H-[1,2']bipyridinyl-5'-yl]-2-(3,5-bistrifluoromethylphenyl)-N-methylisobutylamide (Reference Examples 28) and N-[4-[(R)-2-((S)-4-Benzyl-2-oxo-oxazolidin-3-yl)-1-methyl-2-oxo-ethyl]-4'-(4-fluoro-2-methylphenyl)-3,4,5,6-tetrahydro-2H-[1,2']bipyridinyl-5'-yl]-2-(3,5-bistrifluoromethylphenyl)-N-methylisobutylamide (Reference Examples 29)

A mixture of 2-[5'-{[2-(3,5-bistrifluoromethylphenyl)-2-methylpropionyl]methylamino}-4'-(4-fluoro-2-methylphenyl)-3,4,5,6-tetrahydro-2H-[1,2']bipyridinyl-4-yl]propionic acid ethyl ester (0.50 g aqueous sodium hydroxide solution (1.0 mol/L, 2.0 mL), tetrahydrofuran (2 mL) and methanol (6 mL) was stirred at 140° C. under microwave irradiation for 2 hours. The reaction mixture was cooled to room temperature and hydrochloric acid (1.0 mol/L, 3.0 mL) was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=50/50-0/100) to give 2-5'-{[2-(3,5-bistrifluoromethylphenyl)-2-methylpropionyl]methylamino}-4'-(4-fluoro-2-methylphenyl)-3,4,5,6-tetrahydro-2H-[1,4bipyridinyl-4-yl]propionic acid (0.42 g). To a solution of (S)-4-benzyloxazolidin-2-one (0.06 g) in tetrahydrofuran (4 mL) was added dropwise n-butyllithium (2.65 mol/L in n-hexane solution, 0.12 mL) at −78° C. under an argon gas atmosphere, and the mixture was stirred at the same temperature for 30 minutes to give lithium solution of (S)-4-benzyloxazolidin-2-one. Under an argon gas atmosphere, to a solution of 2-5'- {[2-(3,5-bistrifluoromethylphenyl)-2-methylpropionyl]methylamino}-4'44-fluoro-2-methylphenyl)-3,4,5,6-tetrahydro-2H-[1,2']bipyridinyl-4-yl) propionic acid (0.20 g) and triethylamine (0.04 g) in diethyl ether (4 ml) was added pivaloyl chloride (0.04 g) under ice-cooling, and the mixture was stirred at the same temperature for 1 hour. To the reaction mixture was added dropwise the above lithium solution at −78° C., and the mixture was stirred under ice-cooling for 1 hour. To the reaction mixture was added a saturated aqueous ammonium chloride solution, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90110-10/90). Then, the obtained crude product was purified by column chromatography on silica gel (eluent: n-hexane/ethyl acetate=100/0-50/50). Then, the obtained crude product was purified by preparative thin-layer chromatography (silica gel thickness: 0.5 mm, eluent: n-hexane/ethyl acetate=2/1) to give Reference Examples 28 (0.09 g) and Reference Examples 29 (0.09 g). In the above chromatography, the compound of Reference Examples 28 was in the high polarity side, and the compound of Reference Examples 29 was in the low polarity side.

Reference Example 30

2-[5'-{[2-(3,5-Bistrifluoromethylphenyl)-2-methylpropionyl]methylamino}-6'-cyano-4'-(4-fluoro-2-methyl-phenyl)-3,4,5,6-tetrahydro-2H-[1,2]'bipyridinyl4-yl]propionic acid ethyl ester A suspension of 2-(3,5-bistrifluoromethylphenyl)-N-6-chloro-2-cyano-4-(4-4-fluoro-2-methylphenyl)pyridin-3-yl-N-methylisobutylamide (0.06 g), 2-piperidin-4-yl propionic acid ethyl ester (0.10 g) and potassium carbonate (0.03 g) in dimethyl sulfoxide (1.0 mL) was stirred at 180° C. under microwave irradiation for 2 hours. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on aminopropylated silica gel (eluent: n-hexane/ethyl acetate=90/10-65/35) to give the title compound (0.05 g).

Reference Example 31

5'-{[2-(3,5-Bistrifluoromethylphenyl)-2-methylpropionyl]methylamino}-4'-(4-fluoro-2-methyl phenyl)-4-methyl-3,4,5,6-tetrahydro-2H-[1,2']bipyridinyl-4-yl]acetic acid ethyl ester A mixture of 2-(3,5-bistrifluoromethylphenyl)-N-[6-chloro-4-(4-fluoro-2-methylphenyl)pyridin-3-yl]-N-methylisobutylamide (0.05 g), (4-methylpiperidin-4-yl)acetic acid ethyl ester (0.09 g) and N-methylpyrrolidone (0.5 mL) was stirred at 190° C. under microwave irradiation for 30 minutes. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-60/40) to give the title compound (0.03 g).

Reference Example 32

[5'-{[2-(3,5-Bistrifluoromethylphenyl)-2-methylpropionyl]methylamino}-6'-cyano-4'-(4-fluoro-2-methylphenyl)-4-methyl)4-3,4,5,6-tetrahydro-2H-[12']bipyridinyl-4-yl]acetic acid ethyl ester A suspension of 2-(3,5-bistrifluoromethylphenyl)-N-[6-chloro-4-(4-fluoro-2-methylphenyl)pyridin-3-yl]-N-methylisobutylamide (0.06 g), (4-methylpiperidin-4-yl)acetic acid ethyl ester (0.09 g) and potassium carbonate (0.03 g) in dimethyl sulfoxide (1.0 mL) was stirred at 180° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on aminopropylated silica gel (eluent: n-hexane/ethyl acetate=90/10-65/35) to give the title compound (0.06 g).

Example 1

[5'-{[2-(3,5-Bistrifluoromethylphenyl)-2-methylpropionyl] methylamino}-4-(1-fluoro-2-methylphenyl)-3,4,5,6-tetrahydro-2H-[1,2']bipyridinyl-4-yl]acetic acid To a mixture of [5'-{[2-3,5-bistrifluoromethylphenyl)-2-methylpropionyl]methylamino}-4'-(4-fluoro-2-methylphenyl)-3,4,5,6-tetrahydro-2H-[1,2']bipridinyl-4-yl]acetic acid ethyl ester (0.38 g) in tetrahydrofuran (6 mL), methanol (6 mL) and water (2 mL) was added lithium hydroxide monohydrate (0.12 g) at room temperature, and the mixture was stirred at room temperature overnight. The reaction mixture was neutralized by the addition of 2 mol/L hydrochloric acid (1.5 mL), and the resulting mixture was concentrated under reduced pressure. To the residue was added water, and the resulting mixture was extracted with ethyl acetate. The organic layer was washed with water and brine, and dried over anhydrous magnesium sulfate, and the solvent was removed under reduced pressure to give the title compound (0.37 g).

Example 2

(5'-{[2-(3,5-Bistrifluoromethylphenyl)-2-methylpropionyl]methylamino}-4'-ortho-tolyl-3,4,5,6-tetrahydro-2H-[1,2]bipyridinyl-4-yl)acetic acid To a mixture of [5'-{[2-3,5-bistrifluoromethylphenyl)-2-methylpropionyl]methylamino}-4'-ortho-tolyl-3,4,5,6-tetrahydro-2H-[1,2']bipyridinyl-4-yl]acetic acid ethyl ester (0.30 g) in tetrahydrofuran (4 mL), methanol (2 mL) and water (2 mL) was added lithium hydroxide monohydrate (0.084 g) at room temperature, and the mixture was stirred at room temperature for 3 hours. The reaction mixture was neutralized by the addition of 2 mol/L hydrochloric acid (1.1 mL) and the resulting mixture was concentrated under reduced pressure. To the residue was added water, and the resulting mixture was extracted with ethyl acetate. The organic layer was washed with water and brine, and dried over anhydrous magnesium sulfate, and the solvent was removed under reduced pressure to give the title compound (0.29 g).

Example 3

5'-{[2-(3,5-Bistrifluoromethylphenyl)-2-methylpropionyl]methylamino}-4'-(4-fluoro-2-methyl phenyl)-3,3-dimethyl-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-4'-(4-fluoro-2-methylphenyl)-3,3-dimethyl-3,4,5,6-tetrahydro-2H-[1,2']bipyridinyl-4-yl]acetic acid ethyl ester (0.043 g) in tetrahydrofuran (1 mL), methanol (0.5 mL) and water (0.5 mL) was added lithium hydroxide monohydrate (0.012 g) at room temperature, and the mixture was stirred at room temperature for 3 hours. The reaction mixture was neutralized by the addition of 2 mol/L hydrochloric acid (0.14 mL). Water was added to the mixture, and the resulting mixture was extracted with ethyl acetate. The organic layer was washed with brine, and dried over anhydrous magnesium sulfate, and the solvent was removed under reduced pressure to give the title compound (0.033 g).

Example 4

5'-{[2-(3,5-Bistrifluoromethylphenyl)-2-methylpropionyl]methylamino}-4'-(4-fluoro-2-methyl phenyl)-3-methyl-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-4'-(4-fluoro-2-methylphenyl)-3-methyl-3,4,5,6-tetrahydro-2H-[1,2']bipyridinyl-4-yl] acetic acid ethyl ester (0.040 g) in tetrahydrofuran (1 mL), ethanol (0.5 mL) and water (0.5 mL) was added lithium hydroxide monohydrate (0.011 g) at room temperature, and the mixture was stirred at room temperature for 3 hours. The reaction mixture was neutralized by the addition of 2 mol/L hydrochloric acid (0.13 mL). Water was added to the mixture, and the resulting mixture was extracted with ethyl acetate. The organic layer was washed with brine, and dried over anhydrous magnesium sulfate, and the solvent was removed under reduced pressure to give the title compound (0.035 g).

Example 5

[5'-{[2-(3,5-Bistrifluoromethylphenyl)-2-methylpropionyl]methylamino}-4'-(4-fluoro-2-methyl phenyl)-3-methoxyl-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-4'-(4-fluoro-2-methylphenyl)-3-methoxy-3,4,5,6-tetrahydro-2H-[1,2']bipyridinyl-4-yl]acetic acid ethyl ester (0.025 g) in tetrahydrofuran (1 mL), ethanol (0.5 mL) and water (0.5 mL) was added lithium hydroxide monohydrate (0.006 g) at room temperature, and the mixture was stirred at room temperature for 3 hours. The reaction mixture was neutralized by the addition of 2 mol/L hydrochloric acid (0.075 mL). Water was added to the mixture, and the resulting mixture was extracted with ethyl acetate. The organic layer was washed with brine, and dried over anhydrous magnesium sulfate, and the solvent was removed under reduced pressure to give the title compound (0.021 g).

Example 6

[5'-{[2-(3,5-Bistrifluoromethylphenyl)-2-methylpropionyl]methylamino)}-6'-cyano-4'-(4-fluoro-2-methylphenyl)-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-6-cyano-4'-(4-fluoro-2-methylphenyl)-3,4,5,6-tetrahydro-2H[1,2']bipyridinyl-4-yl] acetic acid ethyl ester (0.02 g) in tetrahydrofuran (0.30 mL), methanol (0.15 mL) and water (0.15 mL) was added lithium hydroxide monohydrate (0.007 g) at room temperature, and the mixture was stirred at room temperature for 2 hours. The reaction mixture was neutralized by the addition of acetic acid. The resulting mixture was extracted with ethyl acetate. The organic layer was washed with brine, and dried over anhydrous magnesium sulfate, and the solvent was removed under reduced pressure to give the title compound (0.02 g).

Example 7

[5'-{[2-(3,5-Bistrifluoromethylphenyl)-2-methylpropionyl]methylamino}-4'-(4-fluoro-2-methylphenyl)-3,4,5,6-tetrahydro-2H-[1,2']bipyridinyl-4-yl]-2-methylpropionic acid A mixture of 2-[5'-{[2-(3,5-bistrifluoromethylphenyl)-2-methylpropionyl]methylamino}-4'-(4-fluoro-2-methylphenyl)-3,4,5,6-tetrahydro-2H-[1,2']bipyridinyl-4-yl]-2-methylpropionic acid ethyl ester (0.14 g), aqueous sodium hydroxide solution (1.0 mol/L, 0.60 mL), tetrahydrofuran (0.6 mL) and methanol (1.8 mL) was stirred at 140° C. under microwave irradiation for 4.5 hours. To the reaction mixture was added aqueous sodium hydroxide solution (2.0 mol/L, 0.50 mL), and the mixture was stirred at 140° C. under microwave irradiation for 2 hours. The reaction mixture was cooled to room temperature and hydrochloric acid (1.0 mol/L, 2.0 mL) was added. The resulting mixture was extracted with ethyl acetate. The organic layer was washed with water and brine, and dried over anhydrous magnesium sulfate, and the solvent was removed under reduced pressure to give the title compound (0.11 g).

Example 8

2-[5'-{[2-(3,5-Bistrifluoromethylphenyl)-2-methylpropionyl]methylamino}-6'-cyano-4'-(4-fluoro-2-methyl-phenyl)-3,4,5,6-tetrahydro-2H-[1,2']bipyridinyl-4-yl]acetic acid To a mixture of 2-[5'-{[2-(3,5-bistrifluoromethylphenyl)-2-methylpropionyl]methylamino}-6'-cyano-4'-(4-fluoro-2-methylphenyl)-3,4,5,6-tetrahydro-2H-[1,2']bipyridinyl-4-yl]propionic acid ethyl ester (0.03 g) in tetrahydrofuran (0.4 mL), methanol (0.2 mL) and water (0.2 mL) was added lithium hydroxide monohydrate (0.008 g) at room temperature, and the mixture was stirred at room temperature overnight. The reaction mixture was neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate/methanol=50/50/0-0/100/0-0/90/10) to give the title compound (0.02 g).

Example 9

5'-{[2-(3,5-Bistrifluoromethylphenyl)-2-methylpropionyl]methylamino}-4'-(4-fluoro-2-methyl phenyl)-4-methyl-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-4'-(4-fluoro-2-methylphenyl)-4-methyl-3,4,5,6-tetrahydro-2H-[1,2']bipyridinyl-4-yl] acetic acid ethyl ester (0.03 g), tetrahydrofuran (0.375 mL), methanol (0.375 mL) and water (0.15 mL) was added lithium hydroxide monohydrate (0.02 g) at room temperature, and the mixture was stirred at room temperature for 3 hours and then at 50° C. for 4 hours. The reaction mixture was cooled to room temperature and hydrochloric acid (2.0 mol/L, 0.2 mL) was added. The resulting mixture was extracted with ethyl acetate. The organic layer was washed with water and brine, and dried over anhydrous sodium sulfate, and the solvent was removed under reduced pressure to give the title compound (0.025 g).

Example 10

[5'-{[2-(3,5-Bistrifluoromethylphenyl)-2-methylpropionyl]methylamino}-6'-cyano-4'-(4-fluoro-2-methylphenyl)-4-methyl-3,4,5,6-tetrahydro-2H-[1,2']bipyridinyl-4-yl]acetic acid To a mixture of [5'-{[2-(3,5-bistrifluoromethylphenyl)-2-methylpropionyl]methylamino}-6'-cyano-4'-(4-fluoro-2-methylphenyl)-4-methyl-3,4,5,6-tetrahydro-2H-[1,2']bipyridinyl-4-yl]acetic acid ethyl ester (0.06 g), tetrahydrofuran (0.50 mL) methanol (0.25 mL) and water (0.25 mL) was added lithium hydroxide monohydrate (0.02 g) at room temperature, and the mixture was stirred at room temperature for 1 hour, and then stirred at 50° C. for 3 hours. The reaction mixture was cooled to room temperature and neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate/methanol=20/80/0-0/100/0-0/90/10) to give the title compound (0.03 g).

Example 11

(S)-2-[5'-{[2-(3,5-Bistrifluoromethylphenyl)-2-methylpropionyl]methylamino}-4'-(4-fluoro-2-methylphenyl)-3,4,5,6-tetrahydro-2H-[1,2']bipyridinyl-4-yl] propionic acid To a mixture of N-[4-[(S)-2-((S)-4-Benzyl-oxo-oxazolidin-3-yl)-1-methyl-2-oxo-ethyl]-4-(4-fluoro-2-methylphenyl)-3,4,5,6-tetrahydro-2H-[1,2]bipyridinyl-5'-yl]-2-(3,5-bistrifluoromethylphenyl)-N-methylisobutylamide (0.08 g) in tetrahydrofuran (1.5 mL) and water (0.5 mL) were added lithium hydroxide monohydrate (0.008 g) and hydrogen peroxide solution (30%, 0.06 mL) under ice-cooling, and the mixture was stirred at the same temperature overnight. To the reaction mixture was added aqueous sodium sulfite solution (10%, 0.75 mL), and the resulting mixture was stirred for 30 minutes. The solvent was removed under reduced pressure. The residue was acidified with hydrochloric acid and the resulting mixture was extracted with ethyl acetate. The aqueous layer was re-extracted with ethyl acetate. The combined organic layer was washed with brine, and dried over anhydrous magnesium sulfate, and the solvent was removed under reduced pressure. The obtained crude product was purified by column chromatography on silica gel (eluent: n-hexane/ethyl acetate=90/10-10/90) to give the title compound (0.014 g).

Example 12

(R)-2-[5'-{[2-(3,5-Bistrifluoromethylphenyl)-2-methylpropionyl]methylamino]}-4'-(4-fluoro-2-methylphenyl)-3,4,5,6-tetrahydro-2H-[1,2]bipyridinyl-4-yl]propionic acid To a mixture of N-[4-[(R)-2-((S)-4-Benzyl-2-oxo-oxazolidin-3-yl)-1-methyl-2-oxo-ethyl]-4'-(4-fluoro-2-methylphenyl)-3,4,5,6-tetrahydro-2H-[1,2]bipyridinyl-5'-yl]-2-(3,5-bistrifluoromethylphenyl)-N-methylisobutylamide (0.04 g) in tetrahydrofuran (0.75 mL) and water (0.25 mL) were added lithium hydroxide monohydrate (0.004 g) and hydrogen peroxide solution (30%, 0.03 mL) under ice-cooling, and the mixture was stirred under the same temperature overnight. To the reaction mixture was added aqueous sodium sulfite solution (10%, 0375 mL), and the resulting mixture was stirred for 30 minutes. The solvent was removed under reduced pressure. The residue was acidified with hydrochloric acid and the resulting mixture was extracted with ethyl acetate. The aqueous layer was re-extracted with ethyl acetate. The combined organic layer was washed with brine, and dried over anhydrous magnesium sulfate, and the solvent was removed under reduced pressure. The obtained crude product was purified by column chromatography on silica gel (eluent: n-hexane/ethyl acetate=90/10-10/90) to give the title compound (0.004 g).

Tables 1 to 7 show the chemical structures of the above compounds of Reference Examples 1 to 32, and the chemical structures and the physical properties of the above compounds of Examples 1 to 12. The abbreviations in these Tables: "Ref No.", "Ex No.", "Str.", "Physical data". "¹H-NMR", "DMSO-d6" and "CDCl₃" represent Reference Example number, Example number, chemical structure, physical property, hydrogen nuclear magnetic resonance spectrum, dimethylsulfoxide-d6 and chloroform-d1, respectively. And, "MS" and "ESI_APCI" represent mass spectrometry and measurement of Electrospray ionization-Atmospheric pressure chemical ionization, respectively.

TABLE 1

| Ref. No. | Str. |
|---|---|
| 1 | 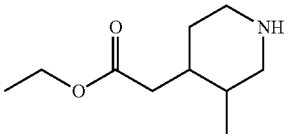 |

TABLE 1-continued

| Ref. No. | Str. |
|---|---|
| 2 | 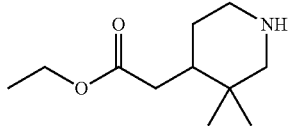 |
| 3 | 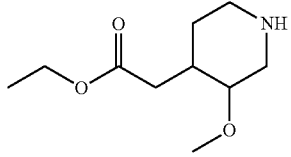 |
| 4 | 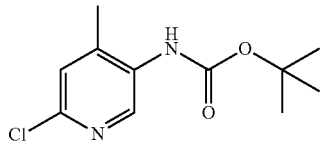 [SMILES: Cc1cc(Cl)ncc1NC(=O)OC(C)(C)C] |
| 5 | 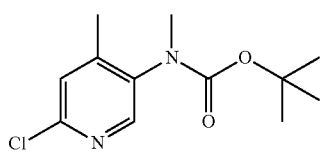 [SMILES: Cc1cc(Cl)ncc1N(C)C(=O)OC(C)(C)C] |
| 6 | 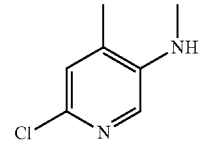 |
| 7 | 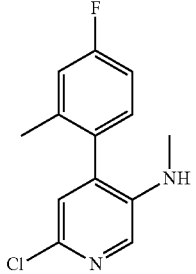 [SMILES: CNc1cnc(Cl)cc1-c1ccc(F)cc1C] |
| 8 | 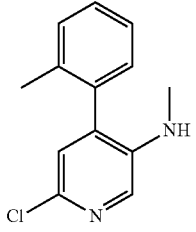 [SMILES: CNc1cnc(Cl)cc1-c1ccccc1C] |

TABLE 2
| Ref. No. | Str. |
|---|---|
| 9 | 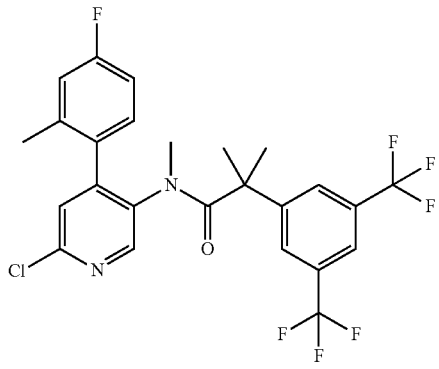 [SMILES: Cc1cc(F)ccc1-c1cc(Cl)ncc1N(C)C(=O)C(C)(C)c1cc(C(F)(F)F)cc(C(F)(F)F)c1] |
| 10 | 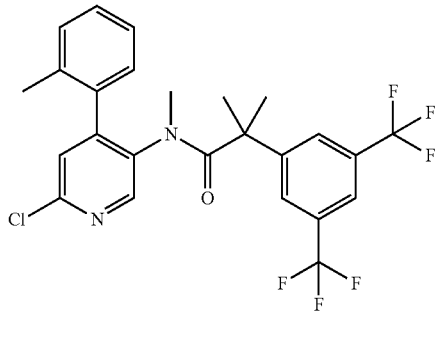 [SMILES: Cc1ccccc1-c1cc(Cl)ncc1N(C)C(=O)C(C)(C)c1cc(C(F)(F)F)cc(C(F)(F)F)c1] |
| 11 | 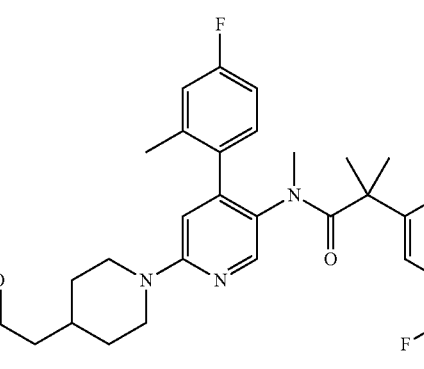 |
| 12 | 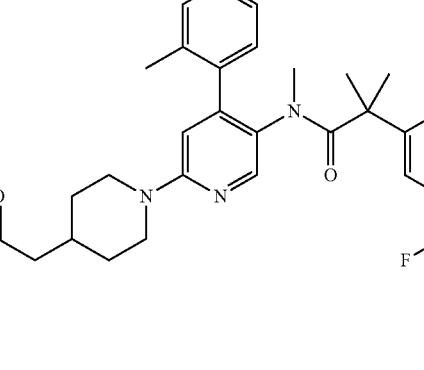 |

TABLE 2-continued
| Ref. No. | Str. |
|---|---|
| 13 | 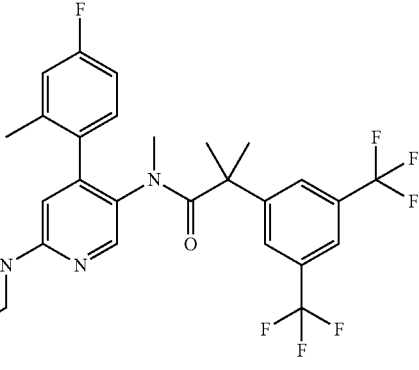 |
| 14 | 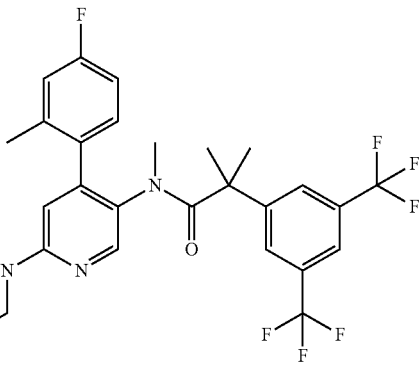 |
| 15 | 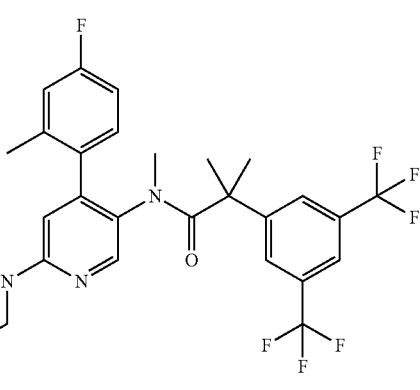 |
TABLE 3
| Ref No. | Str. |
|---|---|
| 16 | 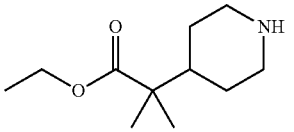 |
| 17 | 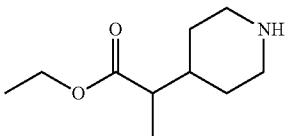 |

TABLE 3-continued

| Ref No. | Str. |
|---|---|
| 18 | ethyl 2-(4-methylpiperidin-4-yl)acetate |
| 19 | 6-chloro-3-nitropicolinonitrile |
| 20 | 3-amino-6-chloropicolinonitrile |
| 21 | 3-amino-4-bromo-6-chloropicolinonitrile |
| 22 | 3-amino-6-chloro-4-(4-fluoro-2-methylphenyl)picolinonitrile |
| 23 | N-(6-chloro-2-cyano-4-(4-fluoro-2-methylphenyl)pyridin-3-yl)-2-(3,5-bis(trifluoromethyl)phenyl)-2-methylpropanamide |
| 24 | N-(6-chloro-2-cyano-4-(4-fluoro-2-methylphenyl)pyridin-3-yl)-2-(3,5-bis(trifluoromethyl)phenyl)-2-methylpropanamide |

TABLE 3-continued
| Ref No. | Str. |
|---|---|
| 25 | 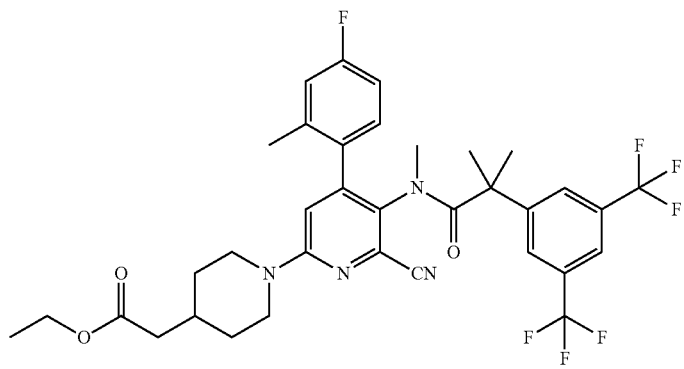 [SMILES: CCOC(=O)CC1CCN(c2cc(-c3ccc(F)cc3C)c(N(C)C(=O)C(C)(C)c3cc(C(F)(F)F)cc(C(F)(F)F)c3)c(C#N)n2)CC1] |
| 26 | 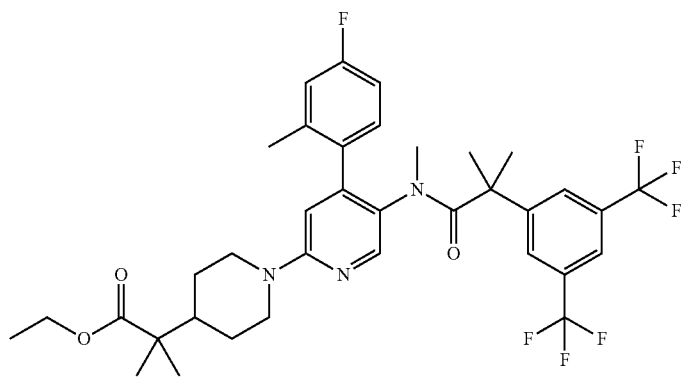 [SMILES: CCOC(=O)C(C)(C)C1CCN(c2cc(-c3ccc(F)cc3C)c(N(C)C(=O)C(C)(C)c3cc(C(F)(F)F)cc(C(F)(F)F)c3)cn2)CC1] |
| 27 | 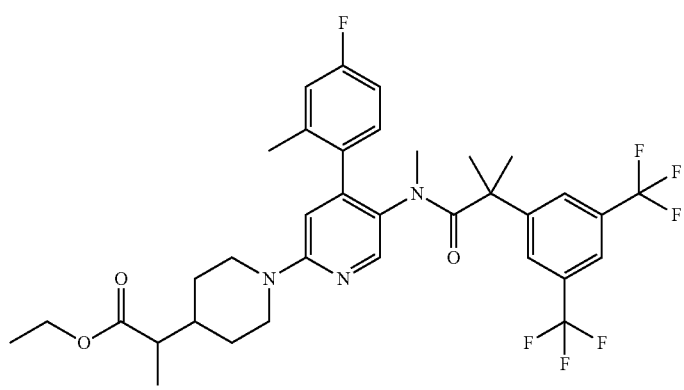 [SMILES: CCOC(=O)C(C)C1CCN(c2cc(-c3ccc(F)cc3C)c(N(C)C(=O)C(C)(C)c3cc(C(F)(F)F)cc(C(F)(F)F)c3)cn2)CC1] |

TABLE 4

| Ref. No | Str. |
|---|---|
| 28 | |
| 29 | |
| 30 | |

TABLE 4-continued

| Ref. No | Str. |
|---|---|
| 31 | |
| 32 | |

TABLE 5

| Ex. No. | Str. | Physical data |
|---|---|---|
| 1 | | $^1$H-NMR δ ppm (DMSO-d6): 1.00-1.60 (9H, m), 1.60-1.80 (2H, m), 1.80-2.00 (1H, m), 2.00-2.40 (7H, m), 2.70-2.90 (2H, m), 4.20-4.40 (2H, m), 6.66 (1H, s), 6.90-7.20 (3H, m), 7.60-7.80 (2H, m), 7.87 (1H, s), 8.03 (1H, s), 12.09 (1H, brs)<br>MS (ESI_APCI, m/z): 640 (M + H)+ |
| 2 | | $^1$H-NMR δ ppm (DMSO-d6): 1.00-1.60 (9H, m), 1.60-1.80 (2H, m), 1.80-2.00 (1H, m), 2.00-2.40 (7H, m), 2.70-2.90 (2H, m), 4.20-4.40 (2H, m), 6.65 (1H, s), 7.00-7.40 (4H, m), 7.60-7.85 (2H, m), 7.86 (1H, s), 8.03 (1H, s), 12.09 (1H, brs)<br>MS (ESI_APCI, m/z): 622 (M + H)+ |

TABLE 5-continued

| Ex. No. | Str. | Physical data |
|---|---|---|
| 3 | | ¹H-NMR δ ppm (DMSO-d6): 0.70-2.80 (25H, m), 3.90-4.10 (1H, m), 4.20-4.50 (1H, m), 6.67 (1H, s), 6.90-7.30 (3H, m), 7.60-7.80 (2H, m), 7.82 (1H, s), 8.03 (1H, s), 12.13 (1H, brs)<br>MS (ESI_APCI, m/z): 668 (M + H)+ |
| 4 | | ¹H-NMR δ ppm (DMSO-d6): 0.75-3.20 (23H, m), 3.80-4.40 (2H, m), 6.60-6.70 (1H, m), 6.90-7.20 (3H, m), 7.60-7.90 (3H, m), 8.03 (1H, s), 12.10 (1H, brs)<br>MS (ESI_APCI, m/z): 654 (M + H)+ |
| 5 | | ¹H-NMR δ ppm (DMSO-d6): 0.75-3.20 (23H, m), 4.10-4.35 (1H, m), 4.40-4.70 (1H, m), 6.60-6.80 (1H, m), 6.90-7.30 (3H, m), 7.60-7.95 (3H, m), 8.03 (1H, s), 12.16 (1H, brs)<br>MS (ESI_APCI, m/z): 670 (M + H)+ |

TABLE 6

| Ex. No. | Str. | Physical data |
|---|---|---|
| 6 | | $^1$H-NMR δ ppm (CDCl$_3$): 1.20-1.75 (8H, m), 1.80-1.90 (2H, m), 2.00-2.75 (9H, m), 2.80-3.00 (2H, m), 4.20-4.40 (2H, m) 6.55-6.65 (1H, m), 6.80-7.25 (3H, m), 7.55-7.85 (2H, m), 7.70-7.80 (1H, m): MS (ESI_APCI, m/z): 665 (M + H)+ |
| 7 | | $^1$H-NMR δ ppm (DMSO-d6): 1.04 (6H, s), 1.10-1.85 (11H, m), 2.00-2.40 (4H, m), 2.60-2.80 (2H, m), 4.30-4.50 (2H, m), 6.65 (1H, s), 6.90-7.25 (3H, m), 7.60-7.80 (2H, m), 7.87 (1H, s), 8.03 (1H, s), 12.15 (1H, brs): MS (ESI_APCI, m/z): 668 (M + H)+ |
| 8 | | $^1$H-NMR δ ppm (CDCl$_3$: 1.15-1.95 (14H, m), 2.05-2.30 (3H, m), 2.30-2.40 (1H, m), 2.40-2.70 (3H, m) 2.80-2.95 (2H, m), 4.25-4.45 (2H, m), 6.55-6.65 (1H, m), 6.80-7.25 (3H, m), 7.60-7.75 (2H, m), 7.70-7.80 (1H, m): MS (ESI_APCI, m/z): 679 (M + H)+ |
| 9 | | $^1$H-NMR δ ppm (DMSO-d6): 1.07 (3H, s), 1.10-1.70 (11H, m) 2.00-2.40 (7H, m), 3.35-3.55 (2H, m), 3.55-3.75 (2H, m), 6.65 (1H, s), 6.80-7.30 (3H, m), 7.55-7.85 (2H, m), 7.88 (1H, s), 8.02 (1H, s), 12.02 (1H, brs): MS (ESI_APCI, m/z): 654 (M + H)+ |

TABLE 6-continued

| Ex. No. | Str. | Physical data |
|---|---|---|
| 10 | 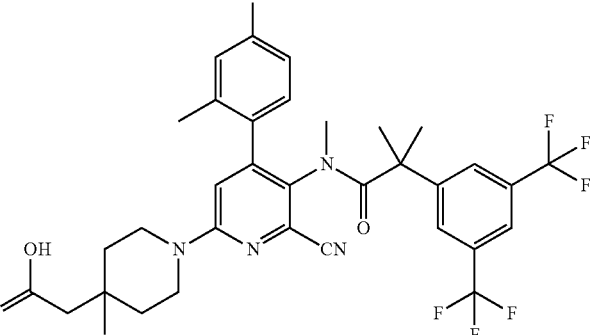 | 1H-NMR δ ppm (CDCl3): 1.15-1.75 (13H, m), 2.05-2.70 (8H, m), 3.40-3.55 (2H, m), 3.65-3.75 (2H, m), 6.55-6.65 (1H, m), 6.80-7.25 (3H, m), 7.55-7.65 (2H, m), 7.75-7.80 (1H, m); MS (ESI_APCI, m/z): 679 (M + H)+ |
| | 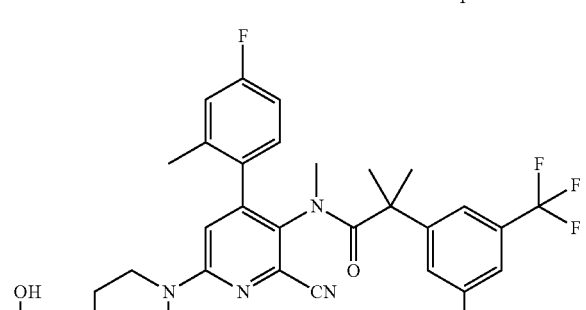 | $^1$H-NMR δ ppm (DMSO-d6) : 1.04 (3H, d, J = 6.8 Hz), 1.10-1.90 (12H, m), 2.05-2.40 (6H, m), 2.85-2.85 (2H, m), 4.25-4.45 (2H, m), 6.65 (1H, s), 6.85-7.25 (3H, m), 7.60-7.80 (2H, m), 7.87 (1H, s), 8.02 (1H, s), 12.10 (1H, brs): MS (ESI_APCI m/z): 654 (M + H)+ |

TABLE 7

| Ex. No. | Str. | Physical data |
|---|---|---|
| 12 | 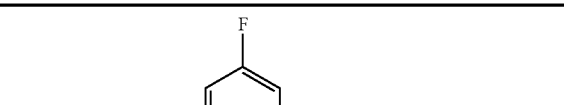 | $^1$H-NMR δ ppm (CDCl$_3$): 1.10-2.70 (21H, m), 2.75-2.95 (2H, m), 4.20-4.45 (2H, m), 6.46 (1H, s), 6.80-7.10 (3H, m), 7.65 (2H, s), 7.76 (1H, s), 7.97 (1H, s): MS (ESI_APCI, m/z): 654 (M + H)+ |

Test Example 1

Affinity for Human NK$_1$ Receptor (1) Preparation of Human NK$_1$ Receptor Expression Vector PCR was performed using human adult normal tissue-derived brain cDNA (BioChain) as the template, with the forward primer of SEQ ID NO:1 and the reverse primer of SEQ ID NO:2, using a PCR enzyme, PrimeSTAR Max DNA Polymerase or PrimeSTAR GXL DNA Polymerase (registered trademark, Takara Bio). The amplified. product was inserted into a plasmid (pCR-BluntII-TOPO (registered trademark), Life. Technologies) using Zero Blunt PCR Cloning Kit (registered trademark, Life Technologies). By a general method, *Escherichia coli* (One Shot TOP10 competent cells, Life Technologies) was transformed by the plasmid into which the amplified product had been inserted. The *Escherichia coli* cells were cultured on an LB agar medium containing 50 μg/mL kanamycin for a day. After the culture, a colony was selected and cultured in an LB medium containing 50 μg/mL kanamycin. After the culture, the plasmid was purified using Quantum Prep Plasmid Miniprep Kit (Bio-Rad). The plasmid was double digested for about two hours using restriction enzymes, XhoI and HindIII (New England Biolabs). Then, electrophoresis using 1% agarose gel was performed, and the fragment that was cleaved was collected and purified using TaKaRa RICO- CHIP (Takara Bio). Separately, a plasmid was also purified from *Escherichia coli* that had been transformed by a vector (pcDNA3.1(−) (registered trademark), Life Technologies), and the plasmid was double digested for about two hours using restriction enzymes. XhoI and HindIII (New England Biolabs). Then, electrophoresis using 1% agarose gel was performed, and the vector that was cleaved was collected and purified using TaKaRa RICOCHIP (Takara Bio). The fragment cut out of pCR-Blunt-II the pcDNA3.1(−) vector treated with the restriction enzymes were ligated using DNA Ligation Kit <Mighty Mix> (Takara Bio). By a general method, *Escherichia coli* (One Shot TOP10 competent cells, Life Technologies) was transformed by the plasmid obtained by the ligation. The *Escherichia coli* cells were cultured on an LB agar medium containing 50 μg/mL ampicillin for a day. After the culture, a colony was selected and cultured in an LB medium containing 50 μg/mL ampicillin, and then the plasmid was purified using Quantum Prep Plasmid Miniprep Kit (Bio-Rad). The protein-encoding nucleotide sequence (SEQ ID NO:3) of the obtained plasmid was completely identical to the nucleotide sequence (NM_001058.3) of human tachykinin receptor 1 (TACR1, NK1 R) registered on a known database (NCBI). Therefore, it was confirmed that the cloned gene sequence was the nucleotide sequence of human $NK_1$ receptor and that the amino acid sequence which would be translated was human $NK_1$ receptor. The pcDNA3.1(−) (registered trademark) into which the nucleotide sequence of SEQ NO:3 was inserted was used as the human $NK_1$ receptor expression plasmid.

(2) Preparation of Human $NK_1$ Receptor-expressing Cells (2-1) Culture of 293T Cells Using a liquid D-MEM (Dulbecco's Modified Eagle Medium) medium (low glucose, containing L-glutamine, Wako Pure Chemical Industries) supplemented with an antibiotic penicillin-streptomycin solution (Life Technologies, final penicillin concentration of 100 U/mL and final streptomycin concentration of 100 μ/mL) and fetal bovine serum (final concentration of 10%), 293T cells (RIKEN) were cultured in an incubator under the condition of 5% $CO_2$ gas at 37° C.

(2-2) Subculture of 293T Cells

Almost confluent cells were washed with PBS (Phosphate Buffered Saline, Wako Pure Chemical Industries), detached using 0.05% trypsin-EDTA (Life Technologies) and suspended in the liquid medium. The cell suspension was diluted with the above liquid medium in such a manner that the spread ratio became 1:10, and then the cells were cultured.

(2-3) Preparation for Human $NK_1$ Receptor-expressing Cells

Continent cells were washed with PBS, detached using 0.05% trypsin-EDTA (Life Technologies) and suspended in a liquid D-MEM medium (low glucose, containing L-glutamine, Wako Pure Chemical Industries) supplemented with fetal bovine serum (final concentration of 10%). The cell suspension was diluted with the liquid medium, and the cells were seeded into the wells of a poly-D-lysine-coated 96-well microplate (BD Biocoat (registered trademark), Nippon Becton Dickinson) at a density of $5\times10^4$ cells/well and a liquid medium volume of 100 μL/well. After seeding, the cells were cultured in an incubator under the condition of 5% $CO_2$ gas at 37° C. for about four to five hours, and the cells to be transfected with the human $NK_1$ receptor expression plasmid were thus prepared.

(2-4) Transfection of Human $NK_1$ Receptor Expression Plasmid into 293T Cells

For the transfection of the human $NK_1$ receptor expression plasmid, Lipofectamine 2000 (registered trademark, Life Technologies) was used. The human $NK_1$ receptor expression plasmid was diluted with Opti-MEM (registered trademark) I Reduced-Serum Medium (Life Technologies) to a concentration resulting in 0.2 μg/25 μL/well. At the same time, Lipofectamine 2000 (registered trademark, Life Technologies) was diluted with Opti-MEM (registered trademark) I Reduced-Serum Medium (Life Technologies) to a concentration resulting in 0.4 μL/25 μL/well and incubated at room temperature for five minutes. After five minutes, to form a complex of human $NK_1$ receptor expression plasmid/Lipofectamine 2000, the diluted human $NK_1$ receptor expression plasmid and the diluted Lipofectamine 2000 were mixed and incubated at room temperature for 20 to 25 minutes. After the incubation, 50 μL/well of the complex solution was added to the cells to be transfected with the human $NK_1$ receptor expression plasmid, and the cells were cultured in an incubator under the condition of 5% $CO_2$ gas at 37° C. for about 48 hours. The cells that were cultured for 48 hours were used for the assays as the human $NK_1$ receptor-expressing cells.

(3) Measurement of Binding Affinity to Human $NK_1$ Receptor (3-1) Preparation of Membrane Fraction from Human $NK_1$ Receptor-expressing Cells Human $NK_1$ receptor-expressing cells were prepared in a 175 $cm^2$ culture flask (Nippon Becton Dickinson). The formation of a complex of the human $NK_1$ receptor expression plasmid and Lipofectamine 2000 was performed by calculating the culture area ratio and increasing the scale of the method described in the above 2-4 by the ratio. The human $NK_1$ receptor-expressing cells were collected in a buffer solution for the membrane fraction preparation (50 mM Tris (Wako Pure Chemical). 120 mM sodium chloride (Wako Pure Chemical Industries), 5 mM potassium chloride (Wako Pure Chemical Industries), 1 mM ethylenediaminetetraacetic acid (Sigma), 0.002 mg/mL chymostatin (Peptide Institute), 0.04 mg/ bacitracin (Wako Pure Chemical Industries), 0.005 mg/mL phosphoramidon (Peptide Institute) and 0.5 mM phenylmethylsulfonyl fluoride (Wako Pure Chemical Industries), pH7.4) and centrifuged at 1,880 g for 10 minutes, and the cell sediment was suspended in the buffer solution for the membrane fraction preparation. After freezing and thawing the cells once, the cells were homogenized using a Dounce-type homogenizer (cooled on ice, 1000 rpm, 20 times). The homogenized cell suspension was centrifuged at 20,000 rpm for 10 minutes, and the supernatant was removed to obtain cell sediment. The cell sediment was suspended again in the buffer solution for the membrane fraction preparation and homogenized using a Dounce-type homogenizer (cooled on ice, 1000 rpm, 30 times). The cell suspension was centrifuged at 20,000 rpm for 10 minutes, and the supernatant was removed to obtain cell sediment. The same homogenization and centrifugation were repeated again, and final cell sediment was obtained. The final cell sediment was suspended in a buffer solution for the receptor binding test (50 mM Tris (Wako Pure Chemical Industries), 3 mM manganese chloride (Wako Pure Chemical Industries), 0.002 mg/mL chymostatin (Peptide Institute), 0.04 mg/bacitracin (Wako Pure Chemical Industries) and 0.02% bovine serum albumin (Sigma), pH 7.4), and the protein concentration was measured using BCA Protein Assay Kit (Pierce).

(3-2) Receptor Binding Test

The buffer solution for the receptor binding test was dispensed to the wells of a 96-well assay plate (Greiner) at 22.5 μL/well. DMSO solutions of a test compound, which were prepared at an 80-time higher concentration using 100% dimethyl sulfoxide (DMSO), were added to the wells at 2.5 μL/well (final concentrations of 1 nM to 100 nM), and the solutions were mixed. As a radiolabeled ligand, $^{125}$I-substance P (Substance P, [$^{125}$I]Tyr$^8$-, PerkinElmer) was used. $^{125}$I-substance P was diluted with the buffer solution for the receptor binding test to a concentration resulting in 125 pmol/25 μL/well and added to the 96-well assay plate, and the solutions were mixed. The membrane fraction prepared from the human NK$_1$ receptor-expressing cells was diluted with the buffer solution for the receptor binding test to a concentration resulting in 8 to 10 μg/well, suspended until the suspension became in such a homogenous state that the suspension could flow through as 27G injection needle smoothly and then added to the 96-well assay plate at 150 μL/well. Then, the plate was incubated at room temperature for 60 minutes while shaking the plate. The reaction solutions were suction-filtered. through a multiscreen 96-well filter plate (Millipore) which had been pre-treated with 0.3% polyethyleneimine, and the reaction was terminated by washing with a washing solution (50 mM Tris and 0.02% bovine serum albumin, pH 7.4) four times. The bottom of the microplate was dried at 60° C., and then 100 μL/well of MicroScint 20 (PerkinElmer) was dispensed to the wells. The top of the plate was sealed with TopSeal A (PerkinElmer), and the plate was shaken for 5 to 10 minutes. Then, the radioactivities were measured with TopCount NXT (registered trademark) (PerkinElmer). The radioactivity of each well was calculated by subtracting the radioactivity of the well to which 10 μM aprepitant was added (non-specific binding). The binding rate (%) of $^{125}$I-substance P=(the radioactivity of the group to which the test compound was added)/(the radioactivity of the group to which the vehicle was added)×100 was calculated. Using analysis software, GraphPad Prism (GraphPad Software), the binding rate (%) was plotted against the concentration of the test compound and linearly approximated, and the concentration required for 50% inhibition, IC$_{50}$, was calculated. These results were shown in Table 8. In the table, Ex. No. means the Example number, and IC$_{50}$ (nM) is the concentration required for 50% inhibition.

(4) Result

TABLE 8

| Ex. No. | IC$_{50}$ (nM) |
|---|---|
| 1 | 2.11 |
| 2 | 2.53 |
| 3 | 4.61 |
| 4 | 3.54 |
| 5 | 3.29 |
| 6 | 2.60 |
| 7 | 4.65 |
| 8 | 2.25 |
| 9 | 2.83 |
| 10 | 3.32 |
| 11 | 1.32 |
| 12 | 7.44 |

As shown in Table 8, it was demonstrated that the compounds of the present invention exhibit a high binding affinity for human NK$_1$ receptor.

Test Example 2

Inhibitory Effect on Human NK$_1$ Receptor
(1) Preparation of Human NK$_1$ Receptor-expressing Cells
Human NK$_1$ receptor-expressing cells were prepared by the same methods as those described in 2-3 and 2-4 of Test Example 1.

(2) Study on Inhibitory Effect on Increase in Intracellular Calcium Concentration The human NK$_1$ receptor-expressing cells were washed with 300 μL/well of a washing solution (20 mM HEPES/Hank's Balanced Salt Solution (HBSS) pH 73). A fluorescent calcium indicator (Fluo-4 Direct Calcium Assay Kit, Life Technologies, containing 0.42 mM probenecid and 0.1% bovine serum albumin, prepared according to the protocol of the product) was added to the wells at 150 μL/well, and the plate was incubated at 37° C. for 30 minutes in an incubator. Then, DMSO solutions of a test compound, which were prepared at an 80-time higher concentration using 100% dimethyl sulfoxide (DMSO), were added to the wells at 2.5 μL/well (final concentrations of 0.1, 1 and 10 μM), and the solutions were mixed. Then, the plate was further incubated at 37° C. for 30 minutes in an incubator. After 30 minutes, the intracellular calcium concentrations were measured immediately.

The intracellular calcium concentrations were each measured as a fluorescent signal using FDSS (registered trademark) 7000 (Hamamatsu Photonics). A substance P (Peptide Institute, Inc.) solution which was prepared at 0.4 μM or 4 μM using an assay buffer (20 mM HEPES/Hank's Balanced Salt Solution (HBSS) pH 7.3, containing 0.1% bovine serum albumin) was added automatically to each well at 50 μL/well (final concentration of 0.1 or 1 μM) 10 seconds after starting reading, and the fluorescent signal was measured up to 120 seconds.

The intracellular calcium concentration (%) of the cells to which a test compound was added was calculated by the equation below, where the fluorescent signal of the group to which the vehicle (DMSO) was added was regarded as 100%, and the fluorescent signal before the addition of substance P was regarded as 0%.

Intracellular calcium concentration(%)=(Fluorescent signal of test compound addition group)/(Fluorescent signal of vehicle addition group)×100

The intracellular calcium concentration (%) calculated was regarded as the remaining agonist activity of substance P (Substance P-Response Remaining: SPRR). These results were shown in Table 9. In the table, Ex. No. means the Example number. SPRR (%) is the value obtained when the concentration of substance P was 1 μM and the concentration of the compound was 0.1 μM.

(3) Results

TABLE 9

| Ex. No. | SPRR (%) |
|---|---|
| 1 | 28 |
| 2 | 54 |
| 3 | 13 |
| 4 | 16 |
| 5 | 49 |
| 6 | 73 |
| 7 | 6 |
| 8 | 69 |
| 9 | 6 |
| 11 | 7 |

As shown in Table 9, it was demonstrated that the compounds of the present invention exhibit a human NK$_1$ receptor antagonist activity.

Test Example 3

Inhibitory Effect on CYP3A4

A dimethyl sulfoxide (DMSO) solution of a test compound with a concentration 1000 times higher than the evaluation concentration was prepared, and a reaction solution was prepared by diluting the solution. Enzyme reaction was performed by incubating in a potassium phosphate buffer solution (pH 7.4) containing 1 nM to 20 µM test compound, 3.2 mM magnesium chloride, 0.2 pmol human CYP3A4 (BD Biosciences), 0.5 mM reduced nicotinamide adenine dinucleotide phosphate (NADPH) and 3 µM Luciferin-IPA (Promega) at 37° C. for 10 minutes. The volume of the reaction solution was 50 µL/well. The 30-minute pre-incubation group was incubated at 37° C. for 30 minutes before adding the substrate, the Luciferin-IPA solution (12.5 µL/well). At the end of the enzyme reaction, 50 µL/well of a Luciferin detection reagent (Promega) was added to the wells, and the plate was left at room temperature for 20 minutes. Then, the emission intensities were measured with Infinite M1000 (TECAN). The enzyme activities (%) relative to the value of the group to which the test compound was not added were calculated. A dose-response curve was drawn using analysis software, GraphPad Prism (GraphPad Software), and the concentration of each compound that exhibited 50% inhibition, $IC_{50}$, was calculated. As a comparative example, aprepitant, which is an $NK_1$ receptor antagonist, was tested in the same manner.

$IC_{50}$ values of the 30-minute pre-incubation groups using the test compounds were measured by the above measurement method, and the results are shown in Table 10. In the table, Ex. No. means the Example number, and $IC_{50}$ (µM) is the concentration required for 50% inhibition.

TABLE 10

| Ex. No. | $IC_{50}$ (µM) |
|---|---|
| 1 | 6.2 |
| 2 | 13 |
| 3 | 3.7 |
| 4 | 4.8 |
| 5 | 5.5 |
| 6 | 2.6 |
| 7 | 4.1 |
| 8 | 1.4 |
| 9 | 6.3 |
| 10 | 3.8 |
| 11 | 4.9 |
| 12 | 4.6 |
| Aprepitant | 0.02 |

It was demonstrated that the CYP3A4-inhibitory activities of the compounds of the present invention are reduced as compared to that of aprepitant. Therefore, it is expected that the compounds of the present invention have fewer drug-drug interactions based on the inhibitory effect on CYP3A4 than aprepitant.

Test Example 4

Effect on Foot-tapping (1) Effect on Foot-tapping

A male gerbil (Japan SLC) was anesthetized with isoflurane, and 0.3 mg/kg of a test compound was administered from the jugular vein. After four hours, GR73632 (5 pmol/5 µl), which is an $NK_1$ receptor agonist, was administered into the cerebral ventricle at the part 1 mm lateral to and 4.5 mm below the bregma in the head, under anesthesia with isoflurane. After the administration, the gerbil was moved to an observation cage, and the foot-tapping period during five minutes after the recovery of the righting reflex was measured. The foot-tapping inhibition rate (%) of each test compound was calculated by the following equation.

Foot-tapping inhibition rate (%)={1−(Foot-tapping period when test compound was administered)/(Foot-tapping period when solvent was administered)}×100

(2) Measurement of Drug Concentrations

After foot-tapping was finished, laparotomy was performed immediately under anesthesia with ether, and a blood sample was taken from the abdominal vena cava. At the same time, the brain was extracted. Through a quantitative analysis using liquid chromatography-mass spectrometry (LC/MS), the concentrations of the test compound in the plasma and the brain were measured.

(3) Results

The effects on foot-tapping were measured by the above test method, and the results are shown in Table 11. In the table, Ex. No. means the Example number. Inhibition (%) is the foot-tapping inhibition rate, and Conc. (nM) is the drug concentration in the brain.

TABLE 11

| Ex. No. | Inhibition (%) | Conc. (nM) |
|---|---|---|
| 1 | 100 | 275 |
| 2 | 81 | 167 |
| 3 | 100 | 262 |
| 4 | 100 | 179 |
| 5 | 97 | 111 |
| 6 | 100 | 243 |
| 8 | 100 | 213 |
| 10 | 100 | 219 |

The compounds of the present invention were penetrated into the central nervous system and exhibited an excellent $NK_1$ receptor antagonist activity also in vivo

Test Example 5

Ferret Pharmacokinetic Test (1) Methods

The test compound solution was prepared by dissolving the test compound in a vehicle (50% N,N-dimethylformamide (Wako Pure Chemical Industries), 30% propylene glycol (Wako Pure Chemical Industries) and 4% 2-hydroxypropyl-β-cyclodextrin (Wako Pure Chemical Industries)). Under anesthesia with isoflurane 0.3 mg/kg of the test compound was intravenously administered to a male ferret (Marshall BioResources Japan) from the jugular vein. In the case of oral administration, 1 mg/kg of the test compound was orally administered to an awake animal. After the administration of the test compound, blood samples were taken sequentially from the brachial cephalic vein, and the concentrations of the test compound in the plasma were measured by a quantitative analysis using liquid chromatography-mass spectrometry (LC/MS).

(2) Results

The pharmacokinetic test in a ferret was tested by the above test method, and the results are shown in Table 12 and Table 13. In the tables, Ex. No. means the Example number. CLtot and Vss are the total body clearance and the steady-state volume of distribution, based on the plasma concentrations in the case of intravenous administration, respectively, $C_{max}$, AUC and BA are the maximum plasma test compound concentration, the area under the plasma test compound concentration-time curve and the bioavailability, in the case of oral administration, respectively,

TABLE 12

| Ex. No. | CLtot (mL/min/kg) | Vss (mL/kg) |
|---|---|---|
| 1 | 0.75 | 336 |

TABLE 13

| Ex. No. | $C_{max}$ (ng/mL) | AUC (ng · min/mL) | BA (%) |
|---|---|---|---|
| 1 | 1,270 | 863,023 | 61 |

As shown in Table 12 and Table 13, the compound of the present invention exhibited an excellent pharmacokinetics.

Test Example 6

Effect on Cisplatin-induced Acute and Delayed Emetic Response
(1) Methods
(1-1) Intravenous Administration Test The test compound solution was prepared by dissolving the test compound in a vehicle (a mixture of 50% N,N-dimethylformamide (Wako Pure Chemical Industries), 30% propylene glycol (Wako Pure Chemical Industries) and 4% 2-hydroxypropyl-β-cyclodextrin (Wako Pure Chemical Industries)). The vehicle only was administered to the control group.

Under anesthesia with isoflurane, 3 mg/kg of the test compound was intravenously administered to a male ferret (Marshall BioResources Japan) from the jugular vein. Cisplatin, which was heated to 40-50° C., was intraperitoneally administered at 5 mg/kg one hour after the drug administration. The ferret was observed for 72 hours from immediately after the cisplatin administration, and the number of retching (periodic abdominal contraction without vomiting of the gastric content) and vomiting was counted.

(1-2) Oral Administration Test

The test compound solution was prepared by dissolving the test compound in a vehicle (1% N-methyl-2-pyrrolidone, 0.5% Tween 80, 20% polyethylene glycol 400 and 78.5% physiological saline). The solvent only was administered to the control group.

The test compound was orally administered to a male ferret (Marshall BioResources Japan). The oral administration was performed every 24 hours at 1 mg/kg three times in total. Cisplatin, which was heated to 40-50° C., was intraperitoneally administered at 5 mg/kg one hour after the first oral administration of the test compound. The ferret was observed for 72 hours from immediately after the cisplatin administration, and the number of retching (periodic abdominal contraction without vomiting of the gastric content) and vomiting was counted.

(2) Results

The results are shown in FIG. 1. In the control group, an increase in the number of retching and vomiting was observed in the acute phase (up to 24 hours after the cisplatin administration) and in the delayed phase (24 hours to 72 hours after the cisplatin administration). In the group to which the compound of Example 1 was intravenously administered and in the group to which the compound was orally administered, the inhibition of the number of retching and vomiting was observed in the acute phase and in the delayed phase.

It was demonstrated that the compound of the present invention has a long-acting medicinal effect and an inhibitory effect on the cisplatin-induced acute and delayed emetic responses.

Test Example 7

Evaluation of hERG Current
(1) Method

A dimethyl sulfoxide (DMSO) solution of the test compound with a concentration 1000 times higher than the evaluation concentration (10 μM) was prepared, and a solution with the a final application concentration was prepared by diluting the solution. The hERG current was measured by a whole-cell method using a patch clamp system, where a cover glass on which hERG channel-expressing human embryonic kidney (HEK) 293 cells were seeded was placed on a perfusion bath and a perfusion solution was caused to flow. The change in the hERG channel-derived current caused by a pulse protocol (holding potential of −80 mV, depolarization pulse of +20 mV for 1.9 seconds, repolarization pulse of −50 mV for 2 seconds, stimulated at intervals of 15 seconds) of data acquisition/analysis software, pCLAMP9 (Axon Instruments, Inc.), was measured. The measurement conditions were a flow rate of about 1.5 mL/min and a temperature of about 33° C. Two wave forms just before applying the test compound and two wave forms immediately after the application for 10 minutes were analyzed, and the statistical analysis was performed. The value before the application of the test compound was regarded as 100%, and the change rate based on the value was determined.

(2) Result

The effect of the test compound on hERG current was evaluated by the above method (the result is shown in Table 14). In the table. Ex. No. means the Example number, and the value is the average±the standard error.

TABLE 14

| Ex. No. | % (n = 3) |
|---|---|
| 1 | 93.9 ± 2.7 |

As shown in Table 14, the compound of the present invention did not cause any change in the hERG current with a statistical significance compared to the vehicle control (0.1% DMSO).

INDUSTRIAL APPLICABILITY

The compounds of the present invention or pharmaceutically acceptable salts thereof have an excellent $NK_1$ receptor antagonist activity, and thus are also useful as an agent for the prevention or treatment of cancer-chemotherapy-induced nausea and vomiting.

SEQUENCE LISTING FREE TEXT

<Sequence Listing 1>
SEQ ID NO:1 is the sequence of forward printer which was used for DNA amplification of SEQ ID NO:3.

<Sequence Listing 2>

SEQ ID NO:2 is the sequence of reverse primer which was used for DNA amplification of SEQ ID NO:3.

<Sequence Listing 3>

SEQ ID NO:3 is the DNA sequence of protein expression site, which was amplified by using primers of SEQ ID NO:1 and 2 for expressing human tachykinin receptor 1.

The invention claimed is:

1. A compound represented by the formula (I):

[Chem.1]

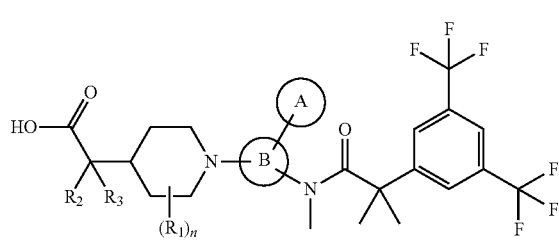

(I)

wherein
ring A is a group represented by the formula:

[Chem. 2]

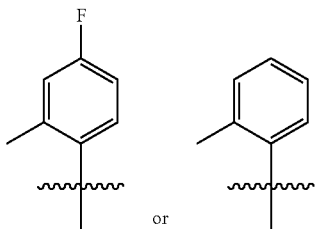

ring B is a group represented by the formula:

[Chem. 3]

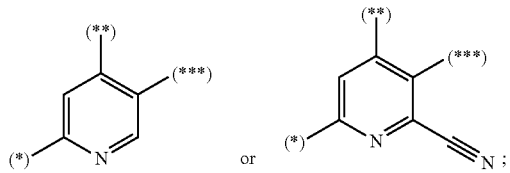

with the proviso that bonds with (*) are bonding site to the formula:

[Chem. 4]

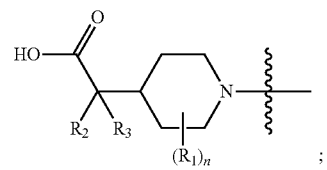

bonds with (**) are bonding site to the ring A;
bonds with (***) are bonding site to the formula:

[Chem.5]

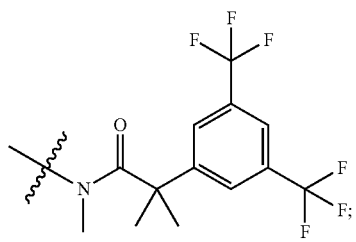

$R_1$ is $C_{1-6}$ alkyl or $C_{1-6}$ alkoxy;

$R_2$ and $R_3$ are each independently a hydrogen atom or methyl;

n is 0, 1, 2, 3, 4 or 5;

or a pharmaceutically acceptable salt thereof.

2. The compound represented by the formula (Ia) according to claim 1:

[Chem.6]

(Ia)

wherein
ring A, $R_1$ and n have the same meaning as described in claim 1;
ring $B^b$ is a group represented by the formula:

[Chem. 7]

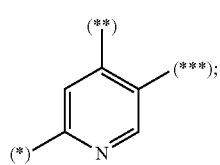

wherein, bond with (\*) is a bonding site to the formula:

[Chem. 8]

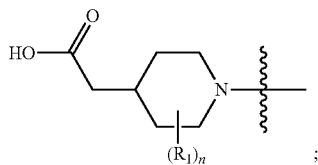

(\*\*) and (\*\*\*) have the same meaning as described in claim 1;
or a pharmaceutically acceptable salt thereof.

3. The compound represented by the formula (Ib) according to claim 2:

[Chem.9]

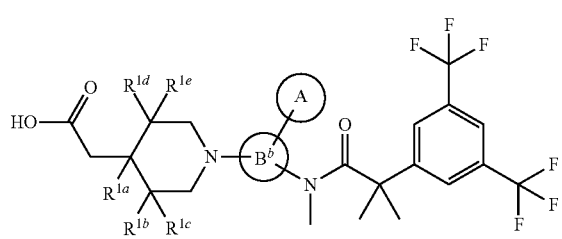

(Ib)

wherein
ring A and ring $B^b$ have the same meaning as described in claim 2;
with the proviso that bond with (\*) is a bonding site to the formula:

[Chem. 10]

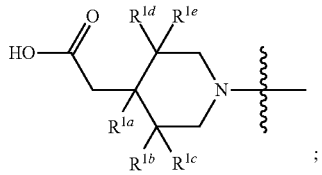

(\*\*) and (\*\*\*) have the same meaning as described in claim 2;
$R^{1a}$, $R^{1b}$, $R^{1c}$, $R^{1d}$ and $R^{1e}$ are each independently any one of a hydrogen atom, methyl or methoxy;
or a pharmaceutically acceptable salt thereof.

4. The compound according to claim 1, wherein ring B is the following formula:

[Chem. 11]

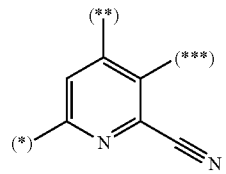

wherein, (\*), (\*\*) and (\*\*\*) have the same meaning as described in claim 1;
or a pharmaceutically acceptable salt thereof.

5. The compound according to claim 4, wherein $R_1$ is methyl, and n is 0 or 1, or a pharmaceutically acceptable salt thereof.

6. A compound represented by the following formula:

[Chem.12]

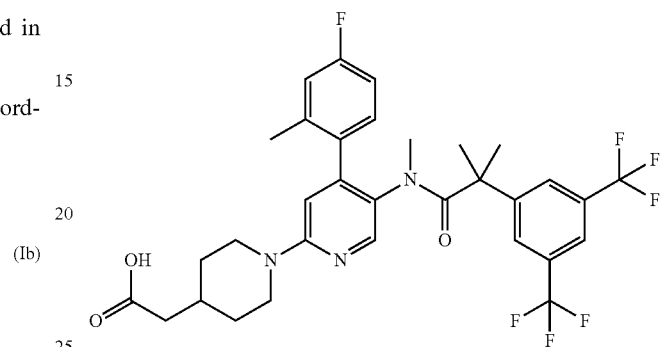

or a pharmaceutically acceptable salt thereof.

7. A compound represented by the following formula:

[Chem.13]

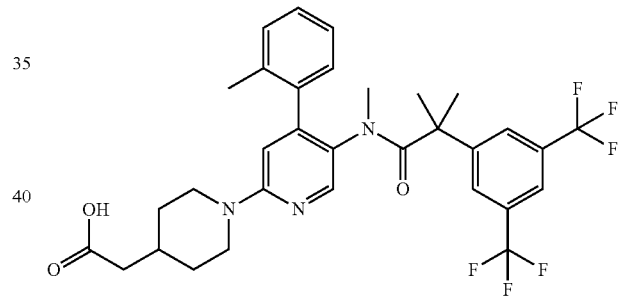

or a pharmaceutically acceptable salt thereof.

8. A compound represented by the following formula:

[Chem.14]

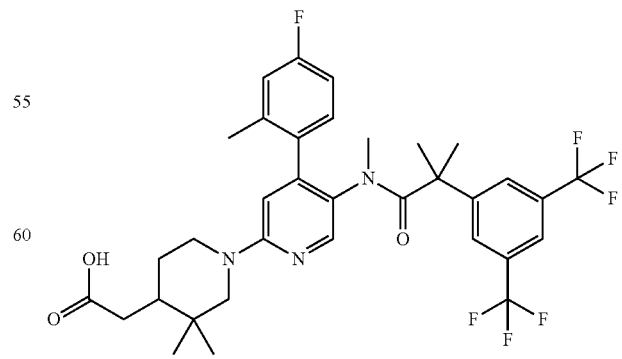

or a pharmaceutically acceptable salt thereof.

9. A compound represented by the following formula:

[Chem.15]

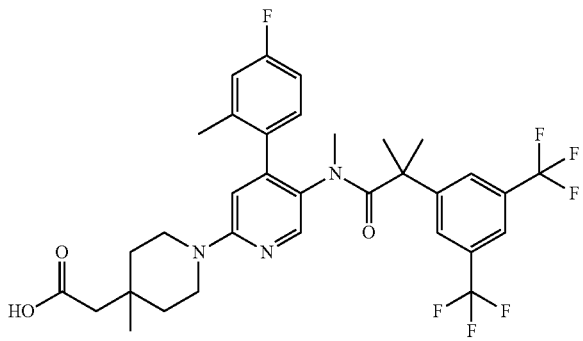

or a pharmaceutically acceptable salt thereof.

10. A compound represented by the following formula:

[Chem. 16]

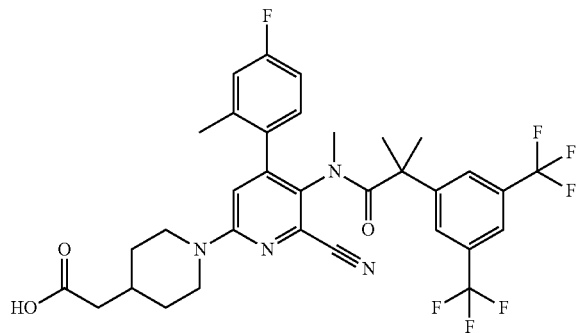

or a pharmaceutically acceptable salt thereof.

11. A pharmaceutical composition comprising as an active ingredient a compound according to claim 1, or a pharmaceutically acceptable salt thereof.

12. A method of reducing or treating cancer-chemotherapy-induced nausea and vomiting, comprising administering the pharmaceutical composition according to claim 11 to a subject in need thereof.

13. A pharmaceutical composition comprising as an active ingredient a compound according to claim 6, or a pharmaceutically acceptable salt thereof.

14. A method of reducing or treating cancer-chemotherapy-induced nausea and vomiting, comprising administering the pharmaceutical composition according to claim 13 to a subject in need thereof.

15. A pharmaceutical composition comprising as an active ingredient a compound according to claim 7, or a pharmaceutically acceptable salt thereof.

16. A method of reducing or treating cancer-chemotherapy-induced nausea and vomiting, comprising administering the pharmaceutical composition according to claim 15 to a subject in need thereof.

17. A pharmaceutical composition comprising as an active ingredient a compound according to claim 8, or a pharmaceutically acceptable salt thereof.

18. A method of reducing or treating cancer-chemotherapy-induced nausea and vomiting, comprising administering the pharmaceutical composition according to claim 17 to a subject in need thereof.

19. A pharmaceutical composition comprising as an active ingredient a compound according to claim 9, or a pharmaceutically acceptable salt thereof.

20. A method of preventing or treating cancer-chemotherapy-induced nausea and vomiting, comprising administering the pharmaceutical composition according to claim 19 to a subject in need thereof.

21. A pharmaceutical composition comprising as an active ingredient a compound according to claim 10, or a pharmaceutically acceptable salt thereof.

22. A method of reducing or treating cancer-chemotherapy-induced nausea and vomiting, comprising administering the pharmaceutical composition according to claim 21 to a subject in need thereof.

\* \* \* \* \*

```
                         SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: forward primer

<400> SEQUENCE: 1
tacctcgaga gatagtaggg ctttaccg                                         28

<210> SEQ ID NO 2
<211> LENGTH: 28
<212> TYPE: DNA
<213> ORGANISM: Artificial Sequence
<220> FEATURE:
<223> OTHER INFORMATION: reverse primer

<400> SEQUENCE: 2
gccaagcttc taggagagca cattggag                                         28

<210> SEQ ID NO 3
<211> LENGTH: 1224
<212> TYPE: DNA
<213> ORGANISM: Homo sapiens

<400> SEQUENCE: 3
atggataacg tcctcccggt ggactcagac ctctcccaa acatctccac taacacctcg       60
gaacccaatc agttcgtgca accagcctgg caaattgtcc tttgggcagc tgcctacacg     120
gtcattgtgg tgacctctgt ggtgggcaac gtggtagtga tgtggatcat cttagcccac    180
aaaagaatga ggacagtgac gaactatttt ctggtgaacc tggccttcgc ggaggcctcc    240
atggctgcat tcaatacagt ggtgaacttc acctatgctg tccacaacga atggtactac    300
ggcctgttct actgcaagtt ccacaacttc tttcccatcg ccgctgtctt cgccagtatc    360
tactccatga cggctgtggc ctttgatagg tacatggcca tcatacatcc cctccagccc    420
cggctgtcag ccacagccac caaagtggtc atctgtgtca tctgggtcct ggctctcctg    480
ctggccttcc cccagggcta ctactcaacc acagagacca tgcccagcag agtcgtgtgc    540
atgatcgaat ggccagagca tccgaacaag atttatgaga aagtgtacca catctgtgtg    600
actgtgctga tctacttcct ccccctgctg gtgattggct atgcatacac cgtagtggga    660
atcacactat gggccagtga gatccccggg gactcctctg accgctacca cgagcaagtc    720
tctgccaagc gcaaggtggt caaaatgatg attgtcgtgg tgtgcacctt cgccatctgc    780
tggctgccct tccacatctt cttcctcctg ccctacatca cccagatct ctacctgaag    840 aagtttatcc agcaggtcta cctggccatc atgtggctgg ccatgagctc caccatgtac    900
aaccccatca tctactgctg cctcaatgac aggttccgtc tgggcttcaa gcatgccttc    960
cggtgctgcc ccttcatcag cgccggcgac tatgagggc tggaaatgaa atccaccgg     1020 tatctccaga cccagggcag tgtgtacaaa gtcagccgcc tggagaccac catctccaca   1080
```

```
gtggtggggg cccacgagga ggagccagag gacggcccca aggccacacc ctcgtccctg    1140
gacctgacct ccaactgctc ttcacgaagt gactccaaga ccatgacaga gagcttcagc    1200
ttctcctcca atgtgctctc ctag                                           1224
```